(12) United States Patent
Baust et al.

(10) Patent No.: US 10,336,984 B2
(45) Date of Patent: Jul. 2, 2019

(54) METHOD OF MOLECULAR STRESS CONTROL

(71) Applicant: CPSI Holdings LLC, Owego, NY (US)

(72) Inventors: John M. Baust, Owego, NY (US); John G. Baust, Candor, NY (US); William L. Corwin, Johnson City, NY (US); Robert G. Van Buskirk, Apalachin, NY (US)

(73) Assignee: CPSI Holdings LLC, Owego, NY (US)

( * ) Notice: Subject to any disclaimer, the term of this patent is extended or adjusted under 35 U.S.C. 154(b) by 20 days.

(21) Appl. No.: 14/819,960

(22) Filed: Aug. 6, 2015

(65) Prior Publication Data

US 2016/0068804 A1 Mar. 10, 2016

Related U.S. Application Data

(63) Continuation of application No. 13/192,722, filed on Jul. 28, 2011, now abandoned.

(60) Provisional application No. 61/368,287, filed on Jul. 28, 2010.

(51) Int. Cl.
| | |
|---|---|
| *C12N 5/00* | (2006.01) |
| *A61K 31/05* | (2006.01) |
| *A61K 31/07* | (2006.01) |
| *A61K 31/34* | (2006.01) |
| *A61K 31/355* | (2006.01) |
| *A61K 31/47* | (2006.01) |
| *A61K 31/593* | (2006.01) |
| *G01N 33/50* | (2006.01) |
| *C12N 5/0735* | (2010.01) |
| *C12N 5/074* | (2010.01) |

(52) U.S. Cl.
CPC ............ *C12N 5/0081* (2013.01); *A61K 31/05* (2013.01); *A61K 31/07* (2013.01); *A61K 31/34* (2013.01); *A61K 31/355* (2013.01); *A61K 31/47* (2013.01); *A61K 31/593* (2013.01); *C12N 5/00* (2013.01); *C12N 5/0606* (2013.01); *C12N 5/0696* (2013.01); *G01N 33/5008* (2013.01); *C12N 2500/02* (2013.01); *C12N 2500/60* (2013.01); *C12N 2502/02* (2013.01); *C12N 2502/45* (2013.01); *C12N 2523/00* (2013.01)

(58) Field of Classification Search
CPC ........ A61K 31/05; A61K 31/07; A61K 31/34; A61K 31/355; A61K 31/47; A61K 31/593; C12N 5/00; C12N 5/0081; C12N 2502/45; C12N 2500/60; C12N 2500/02; C12N 0696; C12N 5/0606; C12N 2523/00; G01N 33/5008
See application file for complete search history.

(56) References Cited

U.S. PATENT DOCUMENTS

| | | | |
|---|---|---|---|
| 6,544,972 B1 | 4/2003 | Steer et al. | |
| 6,632,666 B2 | 10/2003 | Baust et al. | |
| 7,531,327 B2 | 5/2009 | Goldenberg et al. | |
| 2007/0092947 A1 | 4/2007 | Goldenberg et al. | |
| 2008/0269163 A1* | 10/2008 | Sostaric ............ | A61K 31/7004 514/53 |
| 2008/0293699 A1 | 11/2008 | Reed et al. | |
| 2009/0291857 A1 | 11/2009 | Koong et al. | |
| 2010/0215641 A1 | 8/2010 | Roca et al. | |

FOREIGN PATENT DOCUMENTS

WO 2011049680 A1 4/2011

OTHER PUBLICATIONS

Seya et al. "Opposite effects of two resveratrol (trans-3,5,4'-trihydroxystilbene) tetramers, vitisin A and hopeaphenol, on apoptosis of myocytes isolated from adult rat heart." J Pharmacol Exp Ther. Jan. 2009;328(1):90-8.*
Cunha et al. "Glucagon-Like Peptide-1 Agonists Protect Pancreatic β-Cells From Lipotoxic Endoplasmic Reticulum Stress Through Upregulation of BiP and JunB." Diabetes. Dec. 2009; 58(12): 2851-2862.*
Matsuoka and Komoike "Experimental Evidence Shows Salubrinal, an eIF2α0 Dephosphorylation Inhibitor, Reduces Xenotoxicant-Induced Cellular Damage." Int J Mol Sci. Jul. 2015; 16(7): 16275-16287.*
Mathew et al. "Cell preservation in reparative and regenerative medicine: evolution of individualized solution composition." Tissue Eng. Nov.-Dec. 2004;10(11-12):1662-71.*
Corwin et al. "Implications of differential stress response activation following non-frozen hepatocellular storage." Biopreserv Biobank. Feb. 2013;11(1):33-44.*
Cojocari et al. "New small molecule inhibitors of UPR activation demonstrate that PERK, but not IRE1α signaling is essential for promoting adaptation and survival to hypoxia." Radiother Oncol. Sep. 2013;108(3):541-7 (Year: 2013).*

(Continued)

*Primary Examiner* — Titilayo Moloye
(74) *Attorney, Agent, or Firm* — Hoffman Warnick LLC

(57) ABSTRACT

A novel class of agents has been identified to serve as cell-guard agents and/or target-specific supplements to increase cell quality and yield, as well as select for target cell populations. Several additive agents (both natural and synthetic) have been identified, including Vitamin D3, NAC, resveratrol, salubrinal, AKT, and tunicamycin (among others) that hold promise for application in cell models. In one embodiment, hypothermic stress regimes are utilized. In another embodiment, normothermic conditions are utilized while other stressors are tested in the processing. The methods of maintaining mass cell cultures and/or selecting out particular cell populations for further research and clinical use represents an important step in therapeutic discovery.

9 Claims, 30 Drawing Sheets

(56) References Cited

OTHER PUBLICATIONS

Ishikawa et al. "Vertebrate unfolded protein response: mammalian signaling pathways are conserved in Medaka fish." Cell Struct Funct. 2011;36(2):247-59. (Year: 2011).*
Mori K. "Signalling pathways in the unfolded protein response: development from yeast to mammals." J Biochem. Dec. 2009;146(6): 743-50. (Year: 2009).*
Corwin et al "The unfolded protein response in human corneal endothelial cells following hypothermic storage: implications of a novel stress pathway," Cyobiology. 63(1):46-55 (2011).
Reijonen et al., "Inhibition of endoplasmic reticulum stress neuronal cell death and protein aggregation caused by N-terminal mutant huntingtin proteins," Experimental Cell Research. 314:950-60 (2008).
Boyce et al., "A selective inhibitor of elF1-alpha dephosphorylation protects cells from ER stress," Science. 307(5711) 935-9 (2005).
Boyce et al., Supplemental "A selective inhibitor of elF2-alpha dephosphorylation protects cells from ER stress," Science. 307(5711):1-11 (2005).
Kojima et al., "The function of GADD34 is a recovery from a shutoff of protein synthesis induced by ER stress: elucidation by GADD34-deficient mice," FASEB J. 17(11):1573-5 (2003).
Cho et al., "Induction of unfolded protein response during neuronal induction of rat bone marrow stromal cells and mouse embryonic stem cells," Experimental and Molecular Medicine. 41(6):440-52 (2009).
Malhotra et al., "Antioxidants reduce endoplasmic reticulum stress and improve protein secretion," PNAS. 104(47):18525-30 (2008).

Definition of mass. http://dictionary.reference.com/browse/mass. Accessed Aug. 16, 2014.
Definition of cell culture. http://dictionary.reference.com/browselcell%20culture?s=t. Accessed Aug. 16, 2014.
Zheng-Zhi et al., "Edoplasmic reticulum stress induced by tunicamycin and antagonistic effect of tiantai No. 1 on mesenchymal stem cells," Chin J Integr Med. 16(1):41-9 (2010).
Appierto et al., "PLAB induction in fenretinide-induced apoptosis of ovarian cancer cells occurs via a ROS-dependent mechanism involving ER stress and JNK activation," Carcinogenesis. 30(5):824-31 (2009).
Niki et al., "Action of ascorbic acid as a scavenger of active and stable oxygen radicals," Am J Clin Nutr. 54(6 Suppl):1119S-24 (1991).
IUPAC. Compendium of Chemical Terminology, 2nd ed. (the Gold Book). Compiled by A.D. McNaught and A. Wilkinson. Blackwell Scientific Publications, Oxford (1997). ISBN 0-9678550-9-8.
Eibl D, Eibl R. Bioreactors for Mammalian Cells: General Overview Cell and Tissue Reaction Engineering 2008; Springer Berlin Heidelberg 55-82.
Restriction Requirement for U.S. Appl. No. 13/192,722, dated Apr. 23, 2013, 9 pages.
Office Action for U.S. Appl. No. 13/192,722, dated Jul. 17, 2013, 12 pages.
Final Office Action for U.S. Appl. No. 13/192,722, dated Dec. 3, 2013, 25 pages.
Office Action for U.S. Appl. No. 13/192,722, dated Sep. 12, 2014, 35 pages.
Final Office Action for U.S. Appl. No. 13/192,722, dated May 7, 2015, 35 pages.

* cited by examiner

Comparison of C3A Cell Growth Following Post-Freeze Stress with Caspase or Oxidative Stress Modulator Supplementation in the Recovery Culture Media

FIG. 10

| Solution | Agent | Hypothermia | | Normothermia | |
|---|---|---|---|---|---|
| | | C3A | Hepatocyte | C3A | Hepatocyte |
| Media | resveratrol | -- (1d) | ++ (18hr) | -- (7d) | -- (1d) |
| | salubrinal | ++ (1d) | ∅ (18hr) | -- (7d) | + (6d) |
| HBSS | resveratrol | -- (1d) | ++ (18hr) | -- (1d) | -- (1d) |
| | salubrinal | ++ (2d) | ∅ (18hr) | -- (3d) | ++ (3d) |
| ViaSpan | resveratrol | ++ (4d) | ++ (18hr) | N/A | N/A |
| | salubrinal | ++ (4d) | ∅ (18hr) | N/A | N/A |

Key: -- = Negative, + = Positive, ∅ = No Effect, (#d) = # days stress exposure
-- = Highly Negative, ++ = Highly Positive, N/A = Not Available

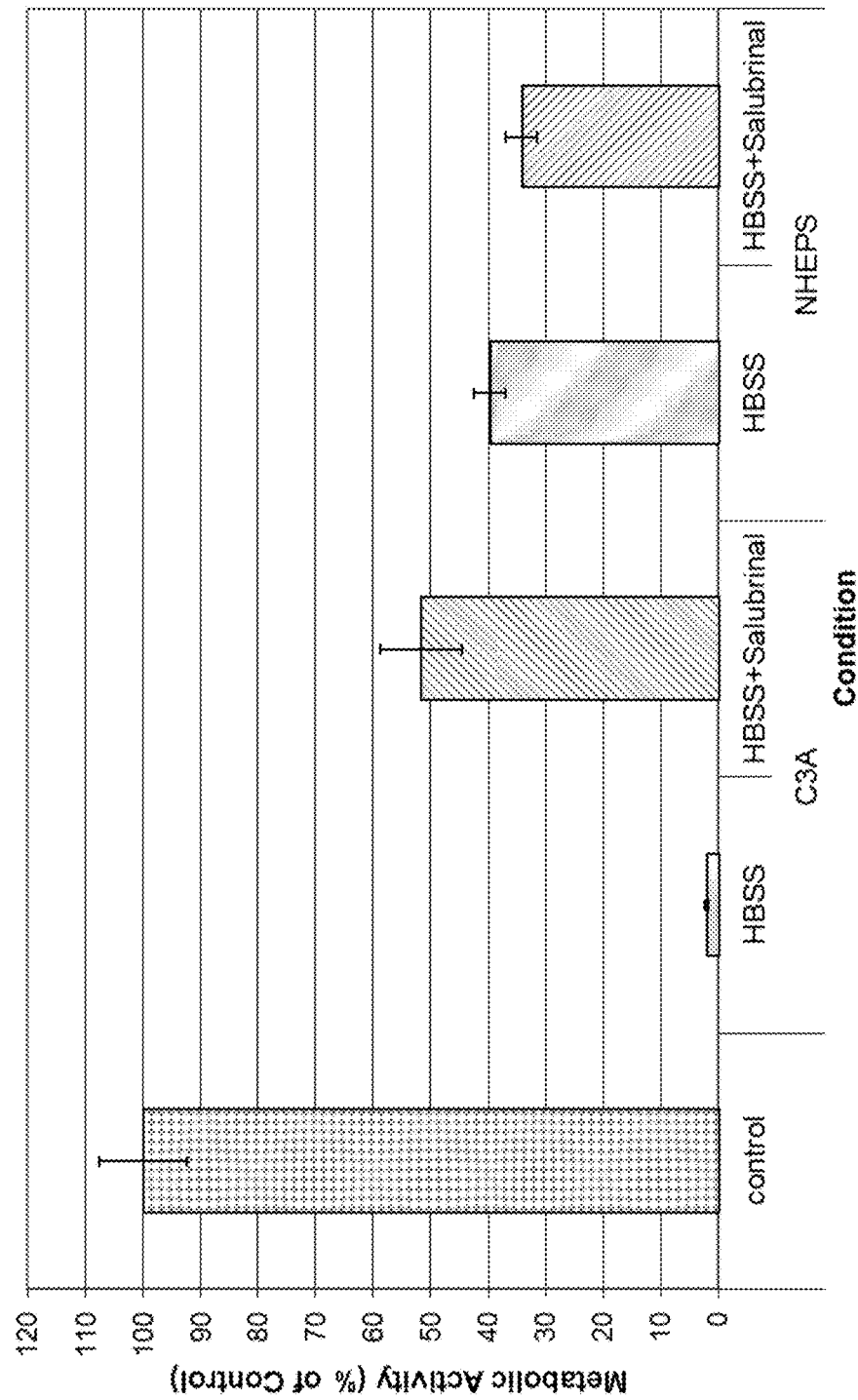

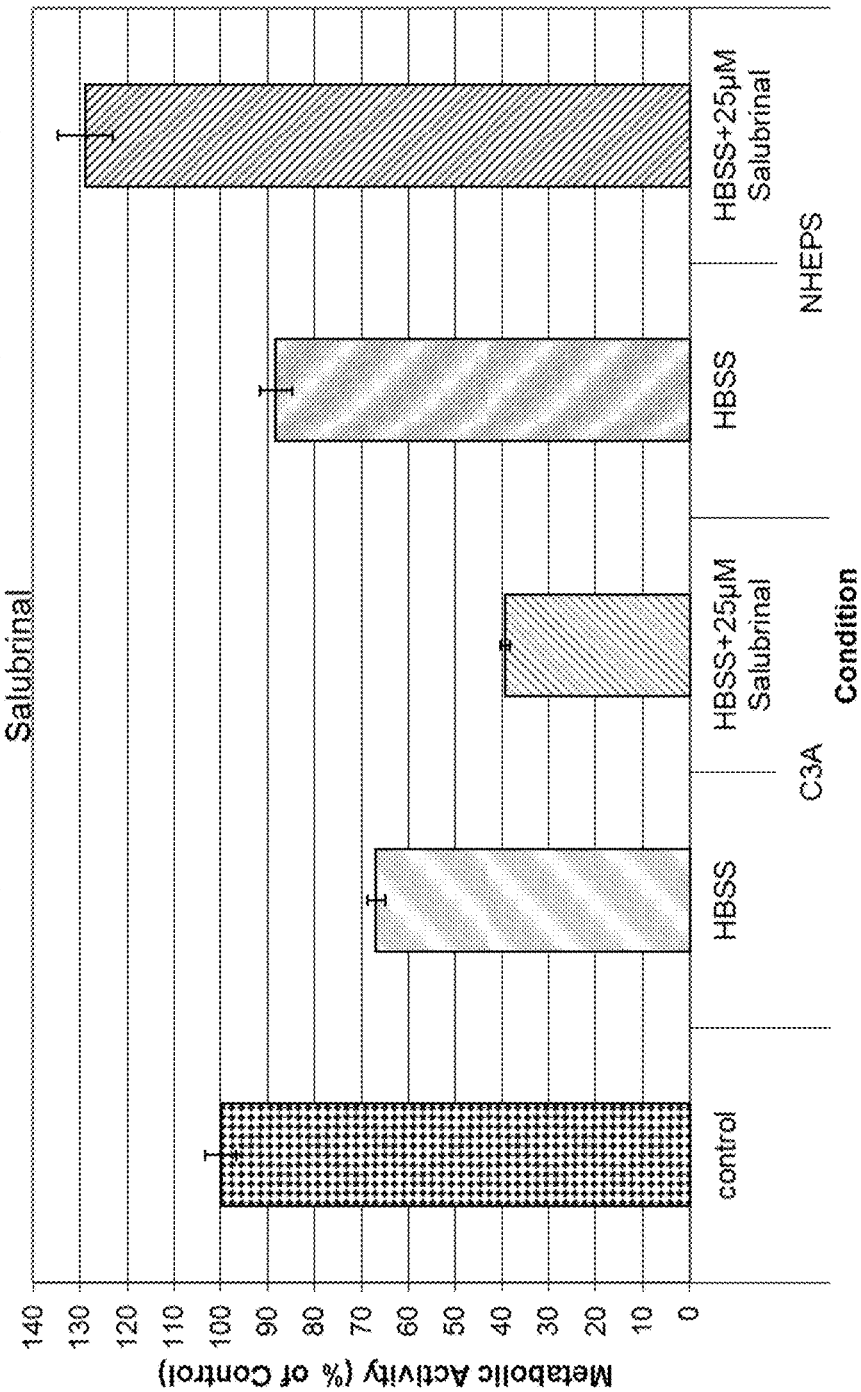

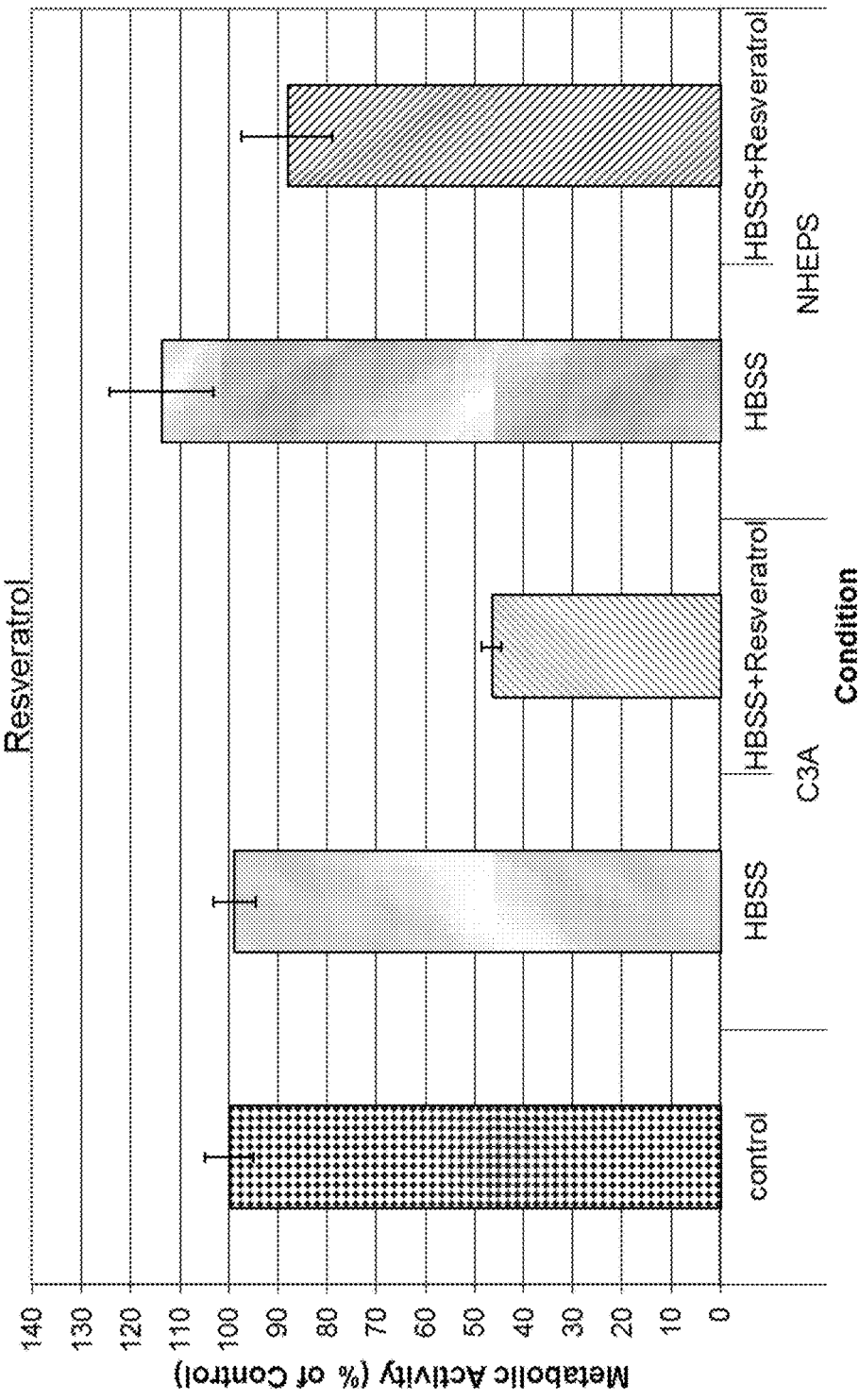

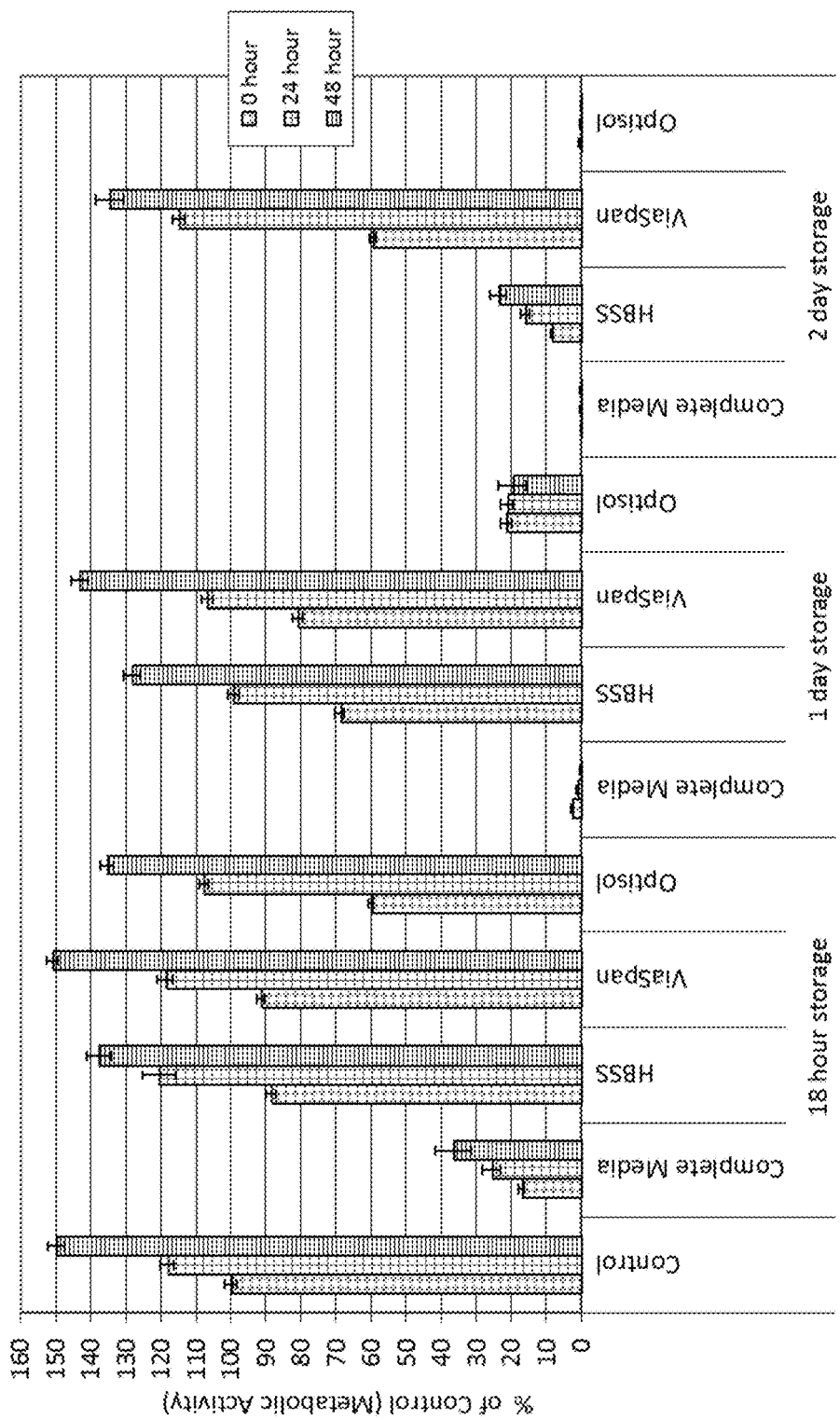

Temporal western blot analysis of apoptotic protein expression in HCEC following 18 hour exposure to 4°C Temporal western blot analysis of ER associated proteins in HCEC following 18 hour exposure to 4°C Temporal Analysis of Cell Death in Cell Subpopulations of HCECs following 24 hours Hypothermic Exposure

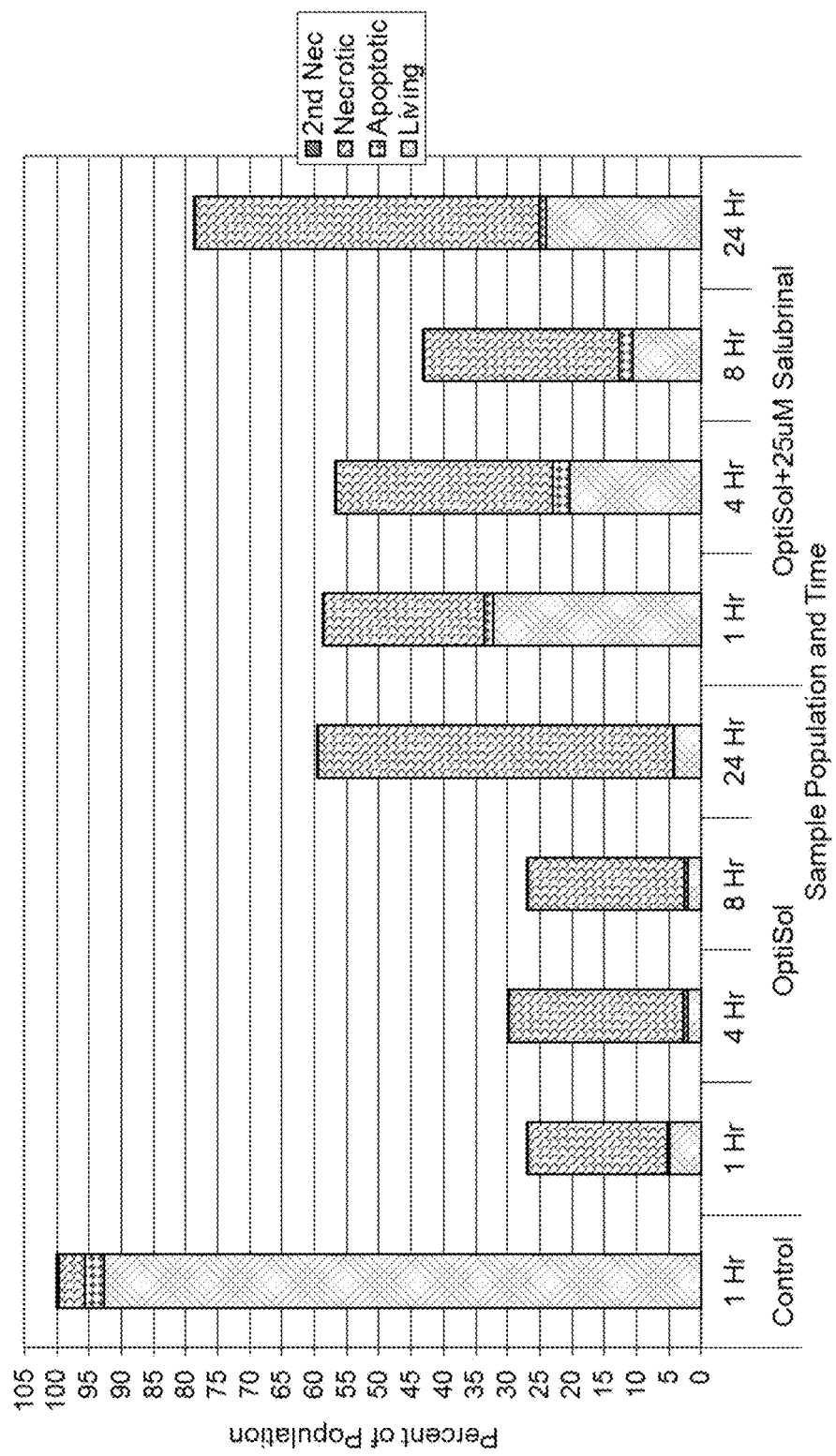

METHOD OF MOLECULAR STRESS CONTROL

CROSS REFERENCE TO RELATED APPLICATIONS

The present application is a continuation of co-pending U.S. application Ser. No. 13/192,722, filed Jul. 28, 2011, which claims priority to U.S. Provisional Patent Application Ser. No. 61/368,287 filed on Jul. 28, 2010. Each of the foregoing applications is incorporated herein by reference in its entirety.

FIELD OF THE INVENTION

The present invention relates generally to the area of cell and molecular biology and, in particular, to supplements for use in bioprocessing.

BACKGROUND OF THE INVENTION

The utilization of in vitro cultured cells in research, medicine, bioprocessing, and bioproduction settings is expanding exponentially. While widely applied and often viewed as common practice, cell culture is a highly variable and dynamic process which has significant impact on the overall quality and performance of the culture. The nuances of cell culture are often addressed with simple procedural or pattern alterations in a laboratory setting, yet these alterations are more often than not incompatible with scale up for successful batch culture of cells in bioprocessing settings.

Mass culture of cellular systems is utilized in settings ranging from drug discovery to bioproduction of therapeutic antibodies to development of new therapeutics and vaccines utilizing cultured cells (cell therapy) to the manufacture of new tissues (tissue engineering). All of these processes require a large number of cells in a similar state thereby requiring mass production and utilization (bioprocessing).

Mass production and utilization of cell media offers a number of technical challenges starting with the simple fact that cell culture is typically characterized by low growth and production rates in comparison with chemical processes. Given the inherent challenges associated with cell culture, processes have evolved to create optimal conditions to maintain cell physiological performance during ex vivo cultivation. In essence, these efforts have been directed at controlling various process parameters to reduce physical and chemical stress, provide proper nutrition to support cell growth and function, reduce bio-waste and toxin accumulation. These efforts have been focused on increasing production, reducing apoptosis, maintaining reproducibility and stability, and maximizing cell culture efficacy.

While cellular bioprocessing has become integral in basic and applied research, as well as in medical therapeutics, a number of significant obstacles have resulted from the stresses created by the conditions used to support proper cell growth and function in an in vitro environment. Alterations in temperature, physical manipulation, pH, osmolality, oxygen and carbon dioxide levels, nutrient levels, chemical stress, waste accumulation, cell interactions and signaling have a significant effect on culture growth and performance. Given the influence of these and other stressors on overall bioproduction efficacy, several approaches to controlling cell culture have evolved including custom and specialized media and bioreactors (culture container) and monitoring engineering. In the area of bioreactors, tremendous effort has been dedicated to the development of devices, containers, pumps, and monitoring sensors in an effort to reduce the variation in the culture conditions, thereby creating a controlled and sustainable environment.

An increased amount of recent activity in culture media formulation has renewed efforts in the biotechnology industry to develop improved culture media formulations to increase product yield while reducing cost. The renewal of these efforts has been spurred on by the recognition that classical culture media developed in the past were primarily designed for simple small scale culture and have proved to be only partially compatible with large scale procedure. As such, much of the classical cell culture media formulation fundamentals fall short in providing a means to support efficient cell bioprocessing. In this regard, challenges remain to develop a specialized culture media that can be customized to individual cell types and culture production processes, procedures and protocols, and the individual response of cells to variances in each of the other parameters associated with cell culture.

Further, in the field of medical diagnostics, including stem cell therapy and cancer, a challenge exists to eliminate or select one or more cell types from a mixed population of cancerous and non-tumorigenic cells without the use of fluorescent tags, chemotherapeutic agents or antibodies. Indeed, cancer stem cells are thought to be present in less than 1% of a stem cell population and antibodies are currently used to purify them.

The use of human embryonic stem cells (hESCs) and induced pluripotent stem cells (iPSCs) for cell therapy will ultimately require selective, non-invasive elimination of the small number of tumorigenic undifferentiated cells known to be present in these populations. While the use of cytotoxic monoclonal antibodies and other transfection systems are currently being developed to address this problem, neither are consistent with FDA regulations for cell therapy. Also, the ability to selectively eliminate cancer cells in a cell culture setting using mutagenic, chemotherapeutic compounds is the basis of cancer drug discovery; but this approach typically requires the use of DNA binding drugs and/or tumor suppressor activators that cannot be used in any procedure that ultimately results in the transfusion of cell products into patients.

A need exists to address this complex issue of media formulation and development and on improving cell culture used in bioprocessing. Bioprocessing needs to be improved and standardized by focusing on all the components of the process including collection, processing, manipulation, culture and selection. Further, bioprocessing must be able to properly maintain cell and tissue specimens such that in their subsequent use or analysis, they retain the characteristics of the system equivalent to their native in vivo state. The impact and importance of these bioprocessing needs will affect the future of medicine.

In addition, a need exists to inhibit cell stress pathways in normal primary cells and tumorigenic cells to either completely eliminate or select the targeted cell type based on the stress pathway inhibitor used. The approach could desirably be used for a variety of applications where the non-chemical/antibody selection of a desired cell phenotype is required such that the product could be used in stem cell therapy, regenerative medicine, cell diagnostics and cancer treatment. A portfolio of therapeutic agents will beneficially be designed for the non-invasive selection and/or elimination of targeted cell types.

The following invention will address the current needs in the industry of bioprocessing and targeted cell selection. The technology bridges the gap between current cell culture technologies (media and devices) and that of the ever-growing demand for increased culture efficiency. Desirably, these improvements will supplement and improve cells undergoing bioprocessing such as in harvesting, bulk culture, fluorescence activated cell sorting (FACS), shipping, transfection and protein bioproduction, advantageously impacting research and medicine overall.

SUMMARY OF THE INVENTION

This invention utilizes unique compound classes to confer protection to cells undergoing bioprocessing events such as harvesting, bulk culture, fluorescence activated cell sorting, shipping, transfection and protein bioproduction. The cell culture media supplements, known as cell-guard and cell-select agents, improve the yield and function of human cells undergoing bioprocessing.

Given the issues associated with bioprocessing and significant loss of processed cells, a series of agents have been identified to serve as cell-guard agents to increase cell quality and yield. The cell-guard formulation is defined by subjecting human cells (and/or various other cells) to specific bioprocessing stresses and then identifying the stress pathways activated. The latter are targeted with inhibitors. Individual pathways include AKT, Unfolded Protein Response (UPR), and other pathways to reduce cell stress response.

As a vitamin or therapeutic adjuvant to cell culture systems, cell-guard can be either a liquid supplement or dissolved tablet, proportional to the cell culture media undergoing various processes. In another aspect, RNAi may be utilized to augment cell-guard function and enhance cell quality. The cell-guard additive reduces the level of cellular loss associated with cell therapy applications and improves viability of media compositions.

In addition, the control of a molecular pathway can also be moderated by using inhibitors to turn on/off a response pathway (e.g. UPR, apoptosis, heat shock, etc.). This mechanism is observed in the use of such inhibitors as caspase, AKT, MPTP, and salubrinal in modulating pathways to improve usability of human cell types. Key cell stress pathways have been identified to target the use of cell-guard additives for growth of hepatocytes, human pancreatic islets, mesenchymal stem cells, cancer stem cells, human corneal endothelial cells (HCEC), hepatoma cell lines (C3A) and kidney cell lines (786-O), among others.

The cell-guard concept has emerged from expertise in cell stress biology. Given the increased activity in cell processing, isolation, and culture, a need to develop enhanced normothermic media additives was identified in order to extend the usable functional life of cells in culture. As the need has now been recognized, various types of supplements have been developed that when added to cells in culture will enhance sample quality during a variety of bioprocessing events. (See FIGS. 1A, 1B, 1C).

For instance, transfused stem cells experience both shear and hypoxia stress, while primary cells experience both mechanical and enzymatic stress during tissue digestion. All of these processes lead to a loss of cell yield and function. Indeed, experts in the field have stated that in many cases only 10% of human primary cells are harvested from whole human tissue with the remainder succumbing to stress-induced cell death. Thus, the improvements in using the cell-guard technology are apparent.

The overall intent of the cell-guard technology is to maintain cells in a more native, reduced stress response molecular-based disposition during bioprocessing. In one aspect, one cell-guard compound enables cells to be maintained in vitro in a more "normal functional state" for extended periods, thereby extending usable life and performance. The approach to developing the cell-guard technology is based on an understanding of the molecular response mechanisms activated within a cell in response to various stressors. It is through an investigation of the cell's stress response that cell-guard is capable of being an additive or supplement compatible with various culture media and bioreactors so that cell stress can be reduced, thus reducing apoptosis and increasing the production (usable) life of existing bioprocessing cultures.

The cell-guard agents are process-matched and cell-matched to protect and/or select particular cells during laboratory and clinical manipulation. The components modulate cell stress and survival pathways.

BRIEF DESCRIPTION OF THE DRAWINGS

The invention is best understood from the following detailed description when read with the accompanying drawing figures. In fact, the dimensions may be arbitrarily increased or decreased for clarity of discussion.

FIG. 1A demonstrates use of the cell supplements in areas of cell and tissue bioprocessing (CCTB); FIG. 1B depicts processes of interest in use of cellular supplements of the invention; FIG. 1C diagrams representative use of cell select ("Cellect") supplements.

FIGS. 10 & 10A-10D depict a comparison of the cell supplements tested in two human liver cell systems, hepatocytes and liver cancer cells (C3A) under a hypothermic stress model and a hypoxic normothermic stress model. FIGS. 10A & 10B depict the hypothermic stress results. FIGS. 10C & 10D depict the hypoxic normothermic stress model.

FIG. 12 shows the viability of HCECs following hypothermic stress (storage at 4° C.).

FIG. 15B is a temporal analysis of cell death in HCECs following 24 hours hypothermic storage using salubrinal.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

The cell-guard product is a cell culture bioreactor media additive that is designed to extend the functional life and production capability of bioreactors. Cell-guard is composed of stress mitigation agents in either a tablet or concentrated liquid format.

Figure 1A:
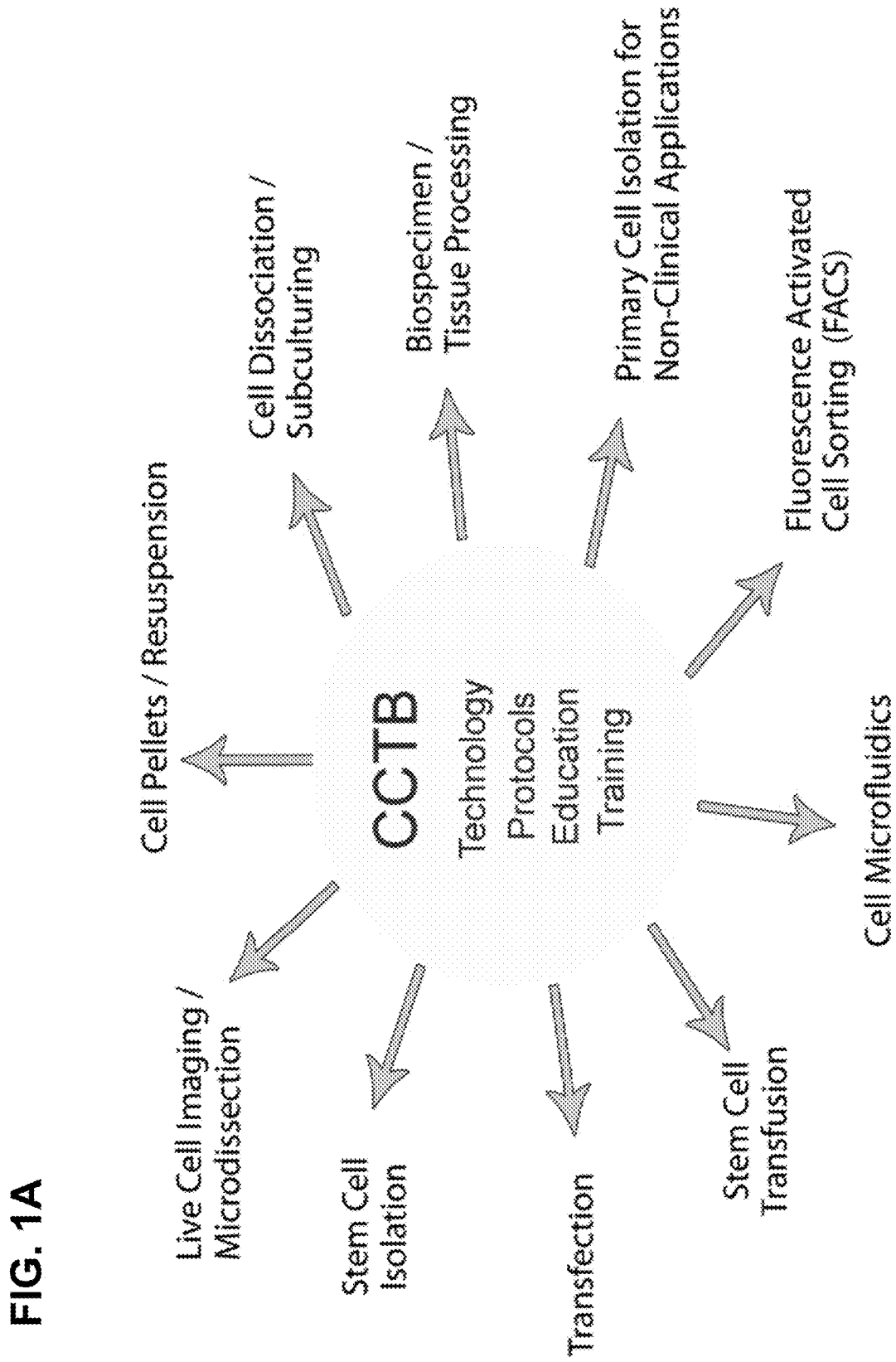
FIGS. 1A-1C depict various applications of interest for use of the invention.
Figure 1B:
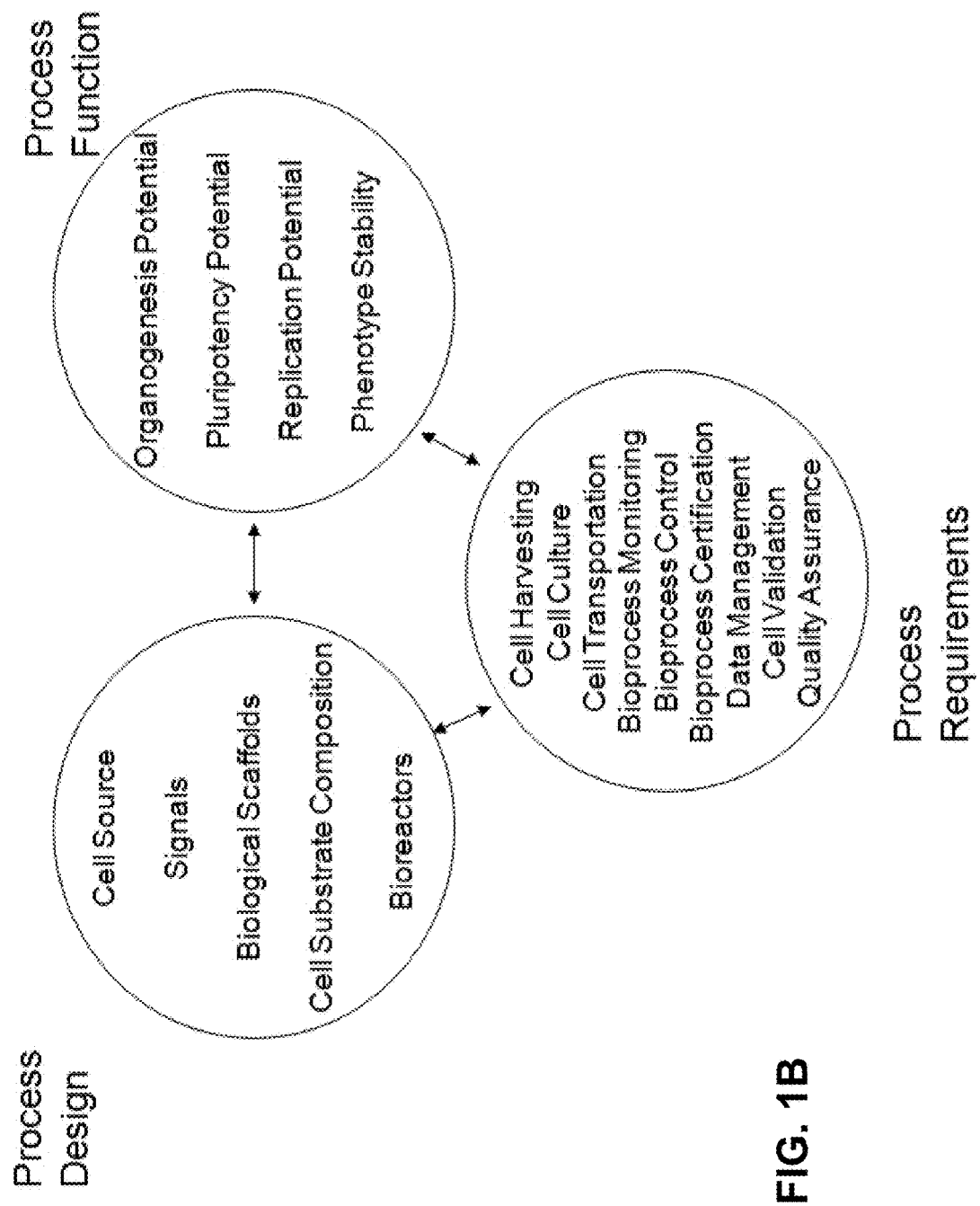
Figure 1C:
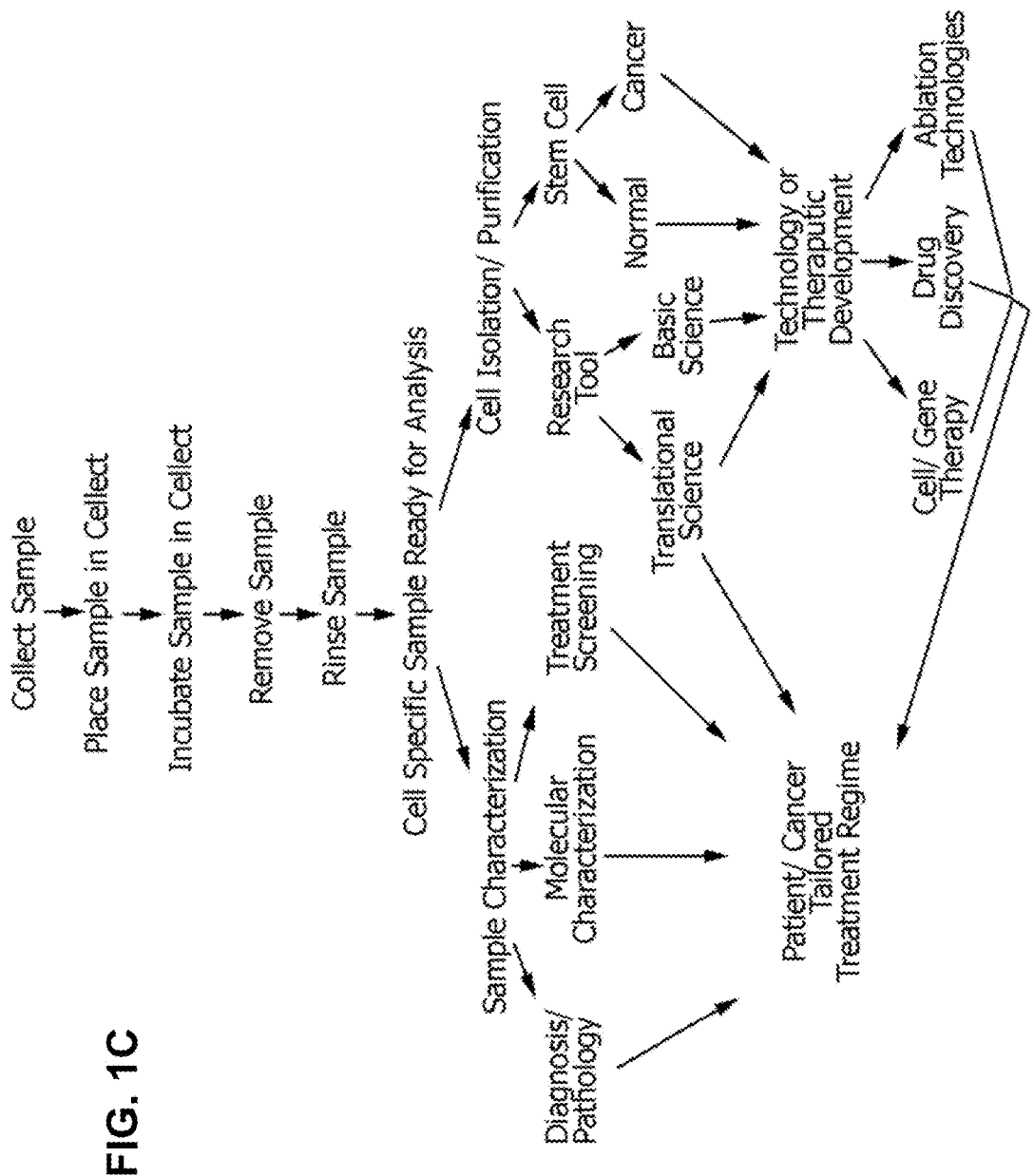

In one embodiment, the cell-guard additive is designed to enhance the lifespan and functionality of cells by reducing stress response in a variety of cell bioprocessing events. Various aspects of the innovative technology development include using a series of cell-guard supplement products in areas of stem cell isolation, live cell microdissection, subculturing, and tissue processing. Various applications in the focus areas are shown in FIG. 1A and FIG. 1C; processes are shown in FIG. 1B. The cell-guard additives are individually designed to manipulate the unique stress response of cells during processing with the goal of improving the bioprocessing of a variety of human cell types. These stresses include exposure to harsh conditions such as microfluidics, transfection, cell sorting, cell selection, and cell jetting (tissue engineering).

Figure 2:
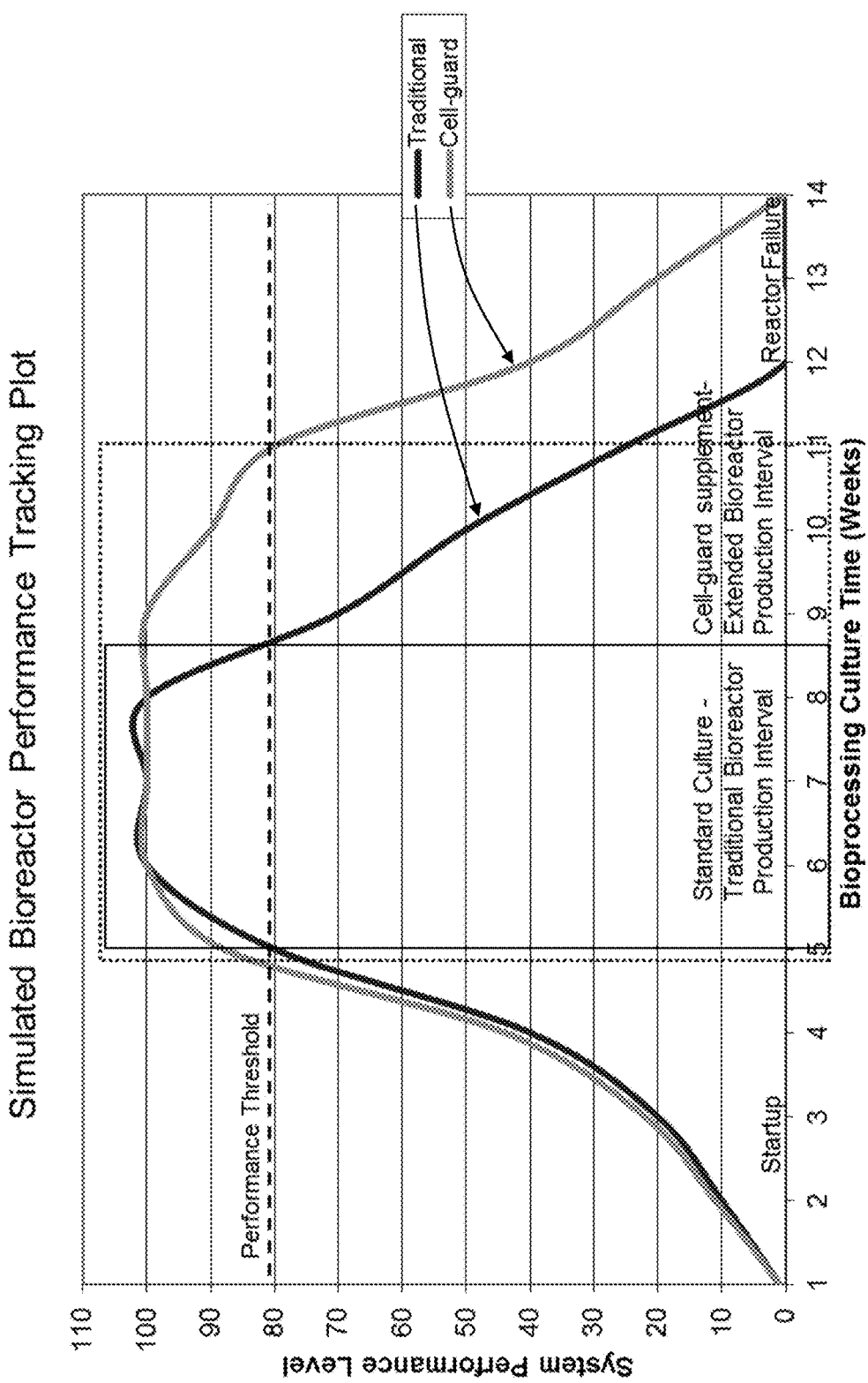
FIG. 2 illustrates simulated bioreactor performance with the use of a cell-guard supplement of the present invention.

As demonstrated in FIG. 2, a 10% improvement in cell culture life during the bioproduction phase results in a 2-3 fold improvement in protein yield. The cost savings alone amounts to about $100,000 per day. Both "natural" and "synthetic" variants of the cell-guard additive have been designed around molecular cell stress activation and effective at targeting specific cells. For exemplary purposes only and not limitation, natural versions of the cell-guard composition include resveratrol and/or vitamin $D_3$. Synthetic variants comprise a variety of synthetic modulators of specific molecular targets including, individually or in combination, AKT, UPR, MPTP, salubrinal (Sal) and ROCK inhibitors.

As illustrated in FIG. 2, a cell-guard additive added to cell culture media improves cell quality (i.e. cell viability, function, and life) by an overall 10-40%. The cell stress pathways have been expanded to address multiple target pathways. To this end, AKT (a serine protein kinase that plays a role in multiple cellular processes such as glucose metabolism, cell proliferation, apoptosis, transcription, and cell migration), MPTP (mitochondrial permeability transition pore), UPR (unfolded protein response), apoptotic, hypoxic, oxidative stress, and anaerobic/aerobic pathways are now included to cover a wide array of agents and stress response pathways for potential modulation by various cell-guard versions to allow for the development of cell and process matched reagents composed of synthetic and/or natural stress inhibitors such as caspase, AKT, MPTP, free radical scavengers, and UPR inhibitors.

In one aspect, the "natural" is of interest to groups who are viewing the use and/or transfusion of iPS (induced pluripotent stem cells) cell-derived hepatocytes or other cell types as a new clinical application. As such, the "natural" cell-guard variant may be less problematic to receive approval through the regulatory process. In another aspect, the "synthetic" variant may be more effective, but given its formulation, much less likely to receive fast-track regulatory approval. Yet the "synthetic" variant would be the variant of choice, for instance, by those groups that process human tissues for the purpose of selling pre-plated cells to the pharmaceutical industry for in vitro toxicology testing.

Modulating Molecular Stress Pathways to Improve Survival of Cells

Vitamin $D_3$

Figure 3:
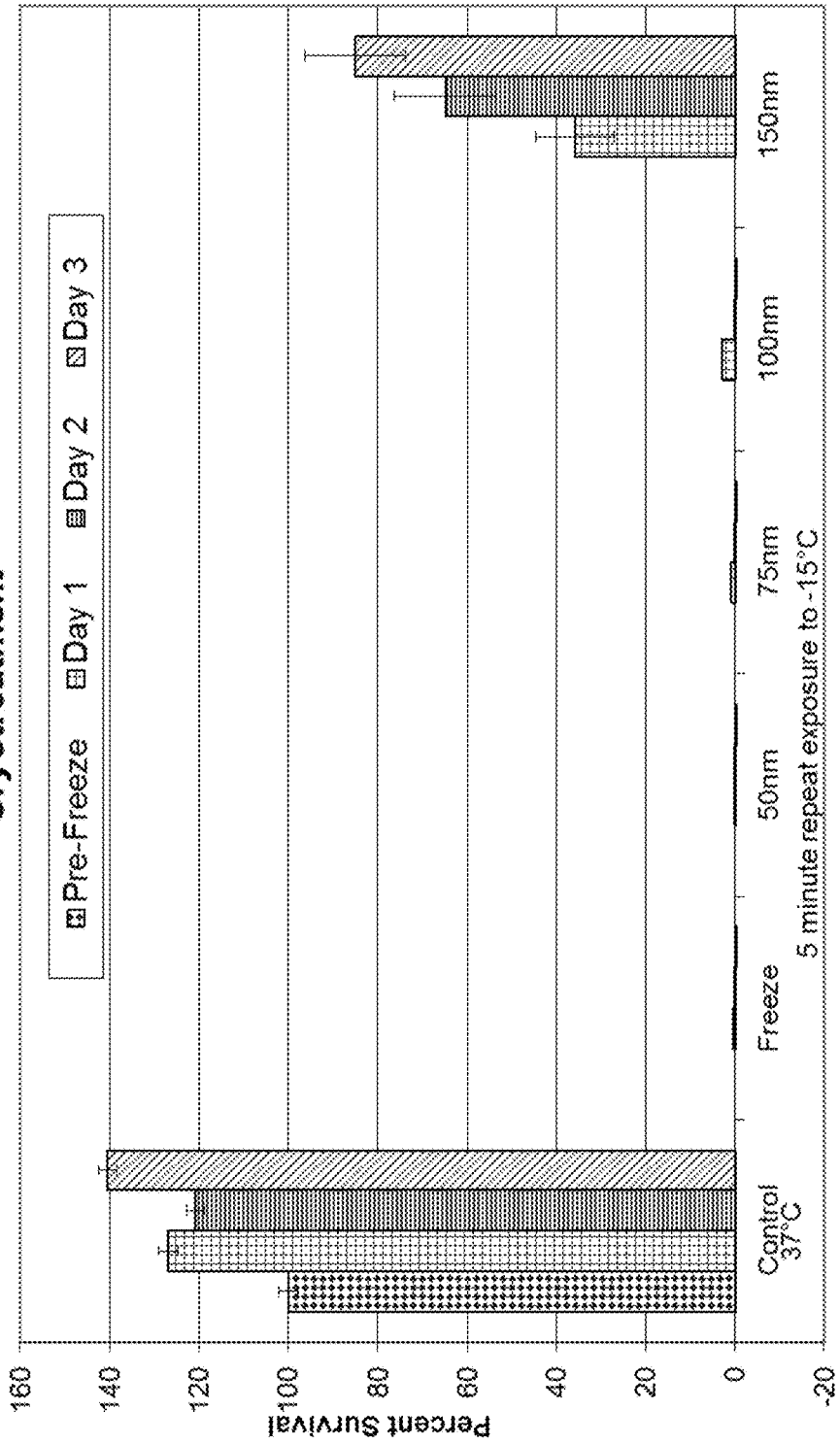
FIG. 3 demonstrates the improved survival of RM-9 prostate cancer cells following stressed conditions.

Experiments have been completed and have expanded the scope of study to (1) include natural agents as part of the formulation and (2) target various stress pathways that may be activated in cells when they are bioprocessed. A variety of agents were used in addition to resveratrol. Of these, Vitamin $D_3$ (i.e. calcitriol) at high doses protects the cells. The data in FIG. 3 demonstrate that Vitamin $D_3$ protects cells such as RM-9 prostate cancer cells (derived from the mouse prostate) under a stress regime. Here, the stress regime included cryotreatment (freezing).

AKT and MPTP Pathways

Figure 4:
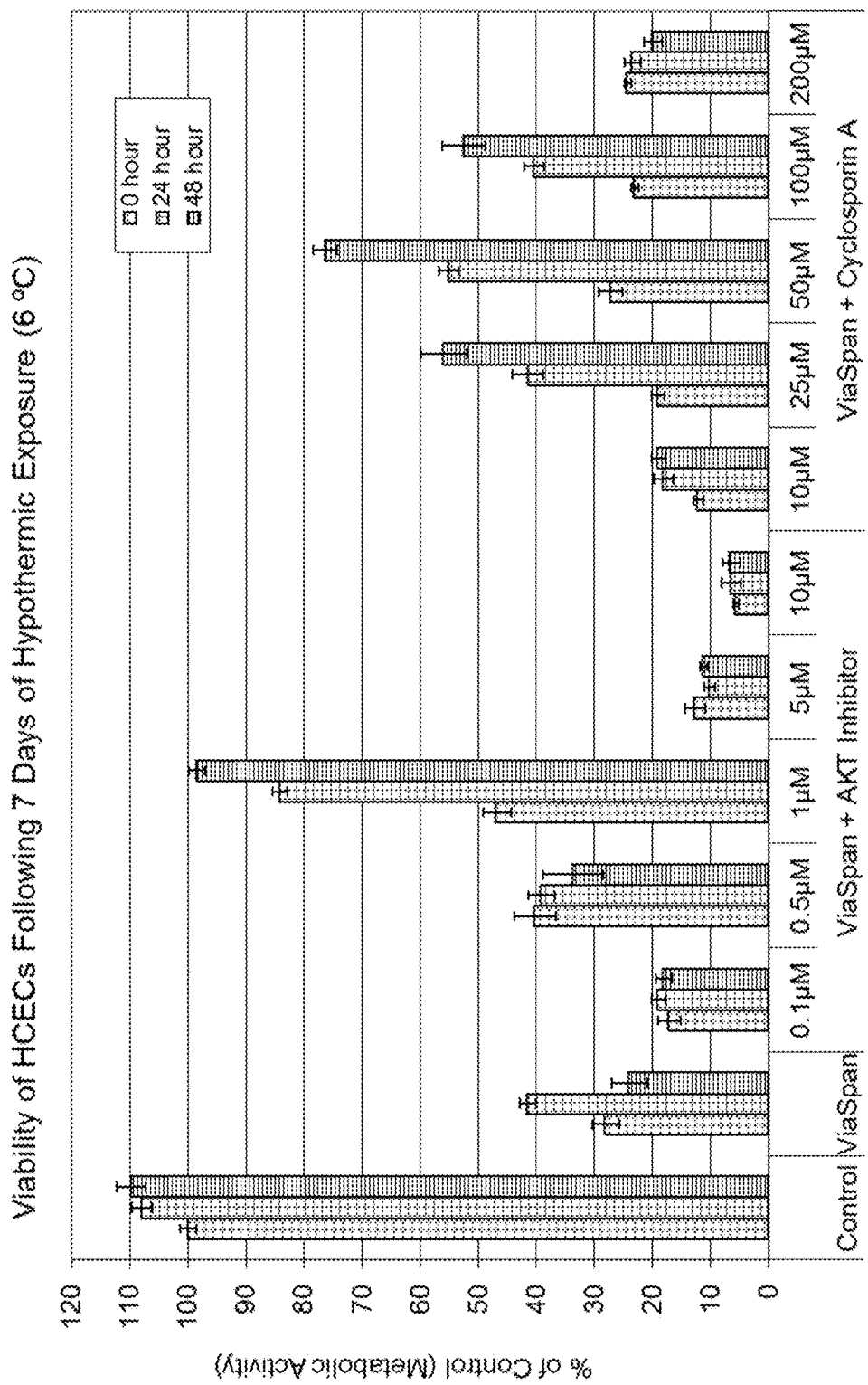
FIG. 4 demonstrates the use of AKT and MPTP inhibitors to enhance cellular function of human corneal endothelial cells (HCECs).

Based on the literature and our knowledge of cell stress biology, cell stress triggers were determined to include the AKT of MPTP pathways. The AKT pathway is a central cell survival pathway that regulates many downstream pathways. The MPTP pathway is the one that, if triggered, can release Cytochrome c to the cytoplasm that leads of apoptosis. As the data in FIG. 4 shows, both AKT and MPTP inhibitors result in enhanced maintenance of cell function of human corneal endothelial cells (HCECs) (National Disease Research Interchange (NDRI): 14CFP5). These agents have been tested on numerous cell types to determine their effects.

UPR Pathways

Figure 5:
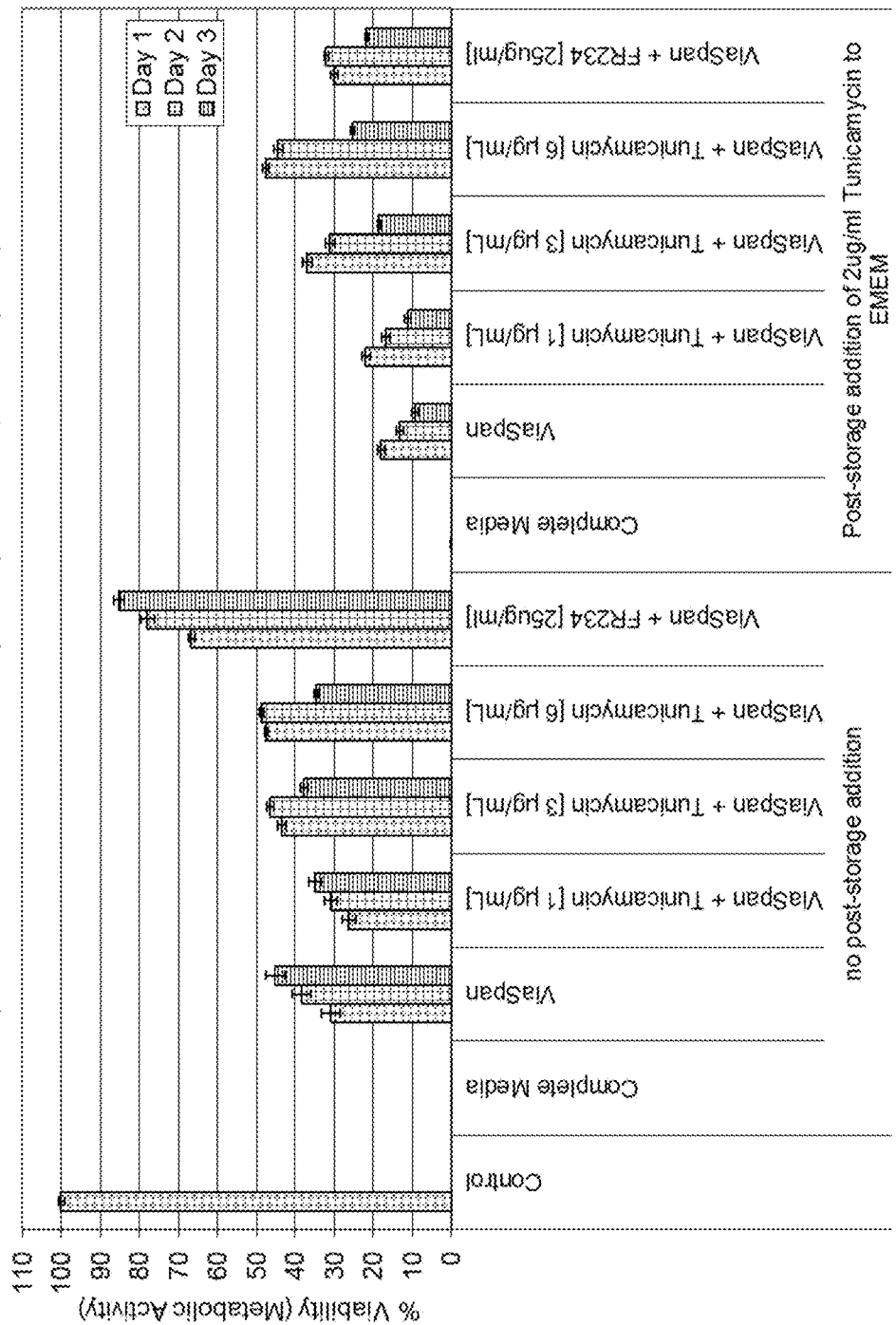
FIG. 5 depicts the viability of human lung fibroblasts (IMR-90) following hypothermic stress conditions with the addition of resveratrol (FR48).

Preliminary studies into Unfolded Protein Response (UPR) pathways in cell death associated with cell stress has provided promising results. The UPR activator, tunicamycin, was applied in a thermal stress regime. In FIG. 5, human lung fibroblasts (IMR-90) were exposed to the cold (4° C.) in cell culture media, Viaspan (with and without tunicamycin), or ViaSpan with DMSO (carrier solution for tunicamycin). The DMSO control acts as a chemical chaperone. It was hypothesized that the addition of tunicamycin would result in an increased level of cell death following thermal stress. The data revealed that UPR activation using tunicamycin resulted in an increase in thermal tolerance.

With this discovery, additional studies were conducted under a more stressful thermal regime designed to completely destroy all cells. As with previous experiments, these studies showed that endoplasmic reticulum (ER)-stress activation by tunicamycin resulted in enhanced thermal tolerance. In subsequent studies, tunicamycin was added subsequent to (rather than during) the cold stress period and compared to samples without addition. (See FIG. 5).

FIG. 5 also depicts the viability of human lung fibroblasts (IMR-90) following two days of cold exposure with the addition of resveratrol (FR234). These studies demonstrated that the post stress addition of tunicamycin resulted in a reduction in cell survival. Further, addition of tunicamycin to samples exposed to resveratrol resulted in the tunicamycin treatment post-cold negating the positive effects of resveratrol (See FIG. 5). Thus, the addition of tunicamycin during the recovery phase had an opposite effect than when added during the cold stress period. Considered together, tunicamycin "sensitizes" the ER-stress program during thermal stress such that many of the ER-sensors are more rapidly up-regulated during recovery, thereby providing a more effective molecular repair response in the cells during the recovery phase. Yet, when tunicamycin is added during the recovery phase, this agent has the predicted lethal effect as described in the UPR literature.

Figure 6:
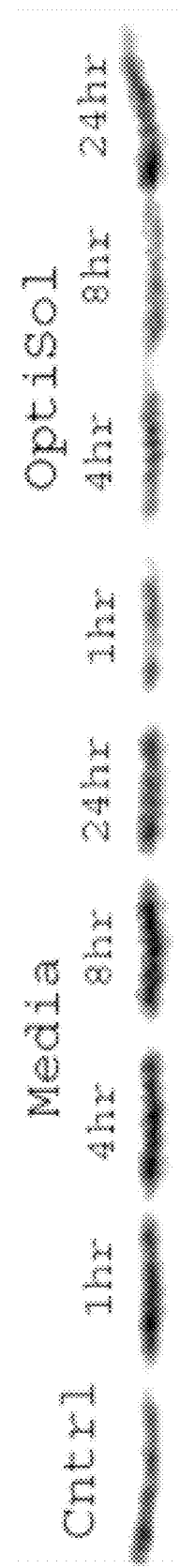
FIG. 6 is a Western blot analysis of a signature UPR protein.

In FIG. 6, experiments using Western blot analysis of binding immunoglobulin protein (BiP) were conducted to evaluate if up-regulation signifies UPR activation in stressed cells. BiP is a luminal endoplasmic reticulum (ER) protein that is believed to serve as an ER stress sensor, triggering the unfolded protein response (UPR). BiP is also known as 78 kDa glucose-regulated protein (GRP-78), or heat shock 70 kDa protein 5 (HSPA5) which is a HSP70 molecular chaperone located in the lumen of the ER that binds newly-synthesized proteins as they are translocated into the ER and maintains them in a state competent for subsequent folding and oligomerization. The synthesis of BiP is markedly induced under conditions that lead to the accumulation of unfolded polypeptides in the ER. The data suggests that the UPR stress pathway plays a pivotal role in cell stress response.

Time course evaluation of HCECs is depicted in FIG. 6 following storage in complete growth media or OptiSol for 18 hours at 4° C. A time dependent and significant increase in BiP levels are noted for these conditions demonstrating the activation of the unfolded protein response (UPR). These data combined with the viability data for this stress regime demonstrate that as sample viability is lost, a profound activation of the UPR is observed.

Hepatoma C3A Cells

The data reveals that the overall impact of the cell-guard with various cell types has varied. It is clear, however, that modulation of the stress response pathway during cell processing results in improved maintenance of cell viability and function (See FIG. 7). It also appears that the positive effects of these agents may be specific to stress regime, concentration and/or the carrier solution.

Figure 7:
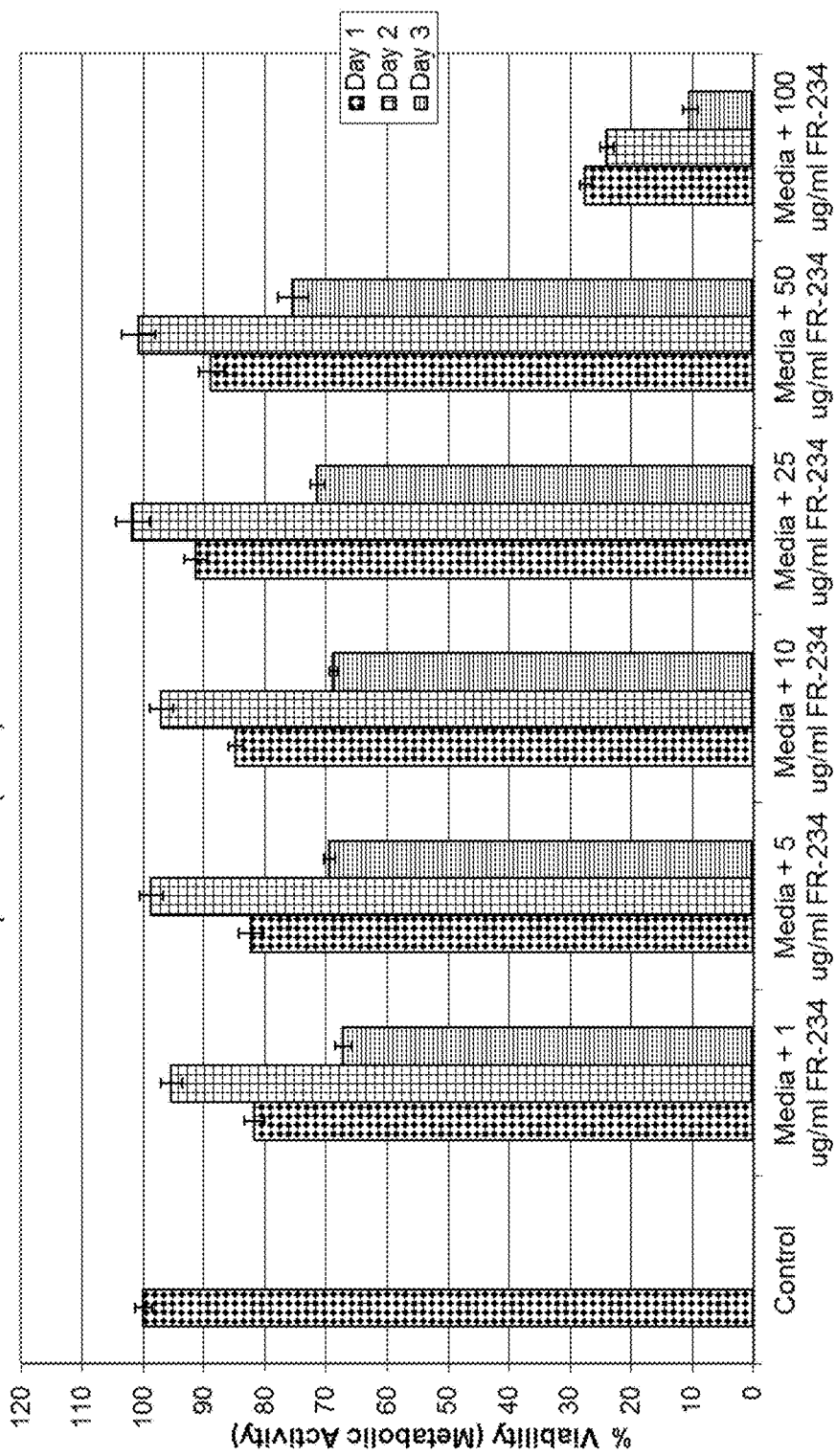
FIG. 7 depicts the effect of stress modulator, resveratrol (FR-234) to human hepatoma (C3A) cell lines under optimal culture conditions.

FIG. 7 assesses the effect of the stress modulator, resveratrol (FR-234), exposure for three days under optimal culture conditions in human hepatoma C3A cell lines. In this graph, C3A cells were stored for three days under optimal culture conditions (37° C., 5% $CO_2$) with a range of FR-234 doses. Cells were removed from storage after three days. Storage solutions were replaced with fresh culture media and viability was assessed at 1, 2, and 3 days post-storage using the metabolic activity indicator, alamarBlue. These data demonstrated that FR-234 addition has a dose dependent effect on stress modulation: the lower doses displayed similar negative effects on post-storage viability; the highest dose (at 100 µg/mL) had a profound negative effect on sample viability.

A number of additional cell models have been analyzed utilizing supplements such as Vitamin $D_3$, N-Acetyl-Cysteine (NAC), ascorbic acid, and specific molecular inhibitors. These experiments are designed to model a number of bioprocessing stress models including hypoxia, nutrient deprivation, sheer stress, pH alterations, and thermal fluctuations. A positive outcome is associated with targeted UPR inhibition as well as with supplemented Vitamin $D_3$.

Figure 8:
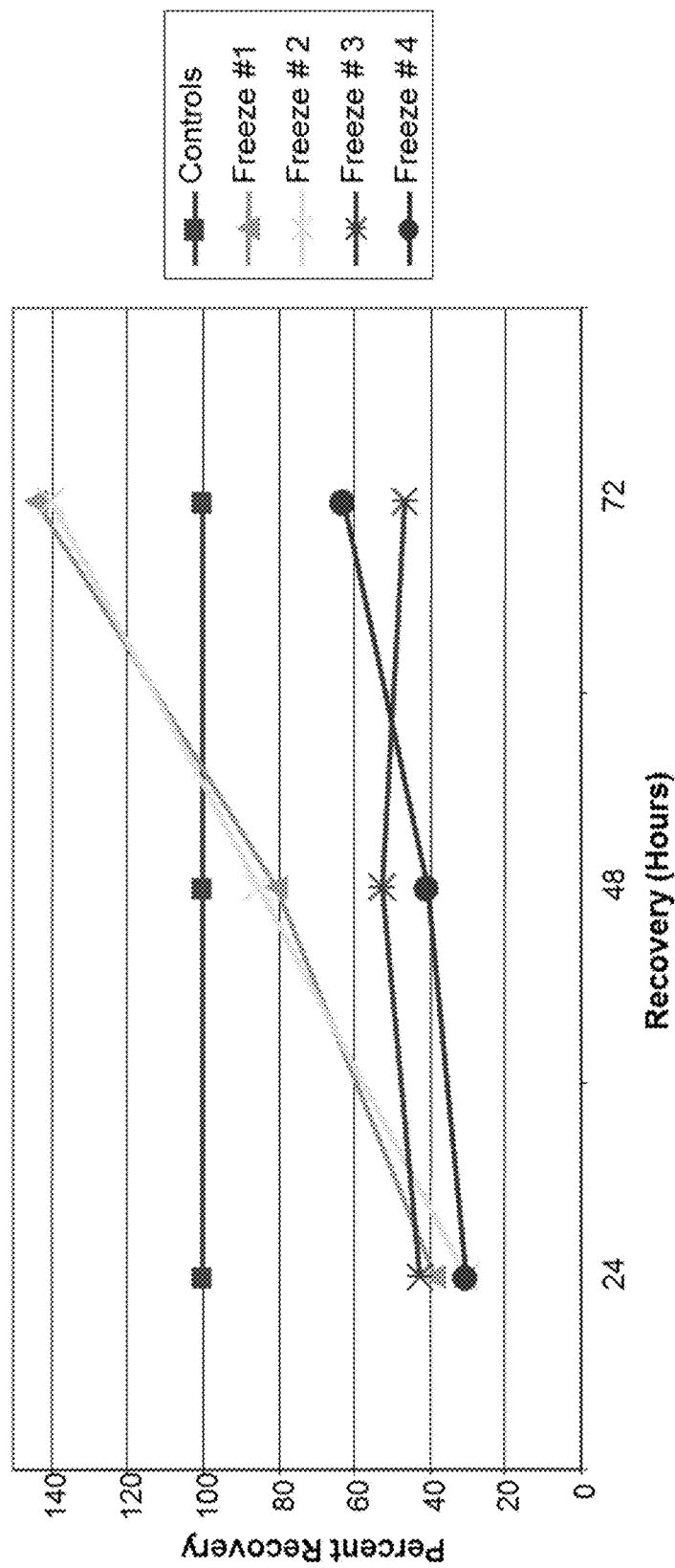
FIG. 8 demonstrates the effect of repeat freeze stress on human hepatoma (C3A) cell lines.

As demonstrated in FIG. 8, a series of experiments using the human hepatoma (C3A), liver cancer cell line, were conducted utilizing a freeze-processing cell banking stress model (cryopreservation). Samples were processed utilizing industry standard media (Roswell Park Memorial Institute, RPMI, media), cryo-protective agents and techniques. Cell survival response curves were plotted against varying concentrations of DMSO. Samples were frozen, thawed, cultured to allow for recovery, and then frozen again. This process was repeated 4 times (e.g. Freeze #1, Freeze #2, Freeze #3, Freeze #4) over experimental periods of several weeks (FIG. 8). The studies revealed that while repeat freezing did not affect initial post-thaw viability, cell functionality and repopulation capacity was altered. Repeat freezing resulted in a loss of the C3A cells ability to grow in culture post-freeze (See FIG. 8, Freeze #3 and Freeze #4).

As the intent of cell-guard is to reduce the negative effects of stress response of cells during normothermic culture processing, a series of studies using the freeze stress model were conducted examining the potential of stress response modulation during recovery culture. The studies examined the effect of modulating the apoptotic cell death mechanism, caspase cascade, as well as mitochondrial oxidative stress pathways. While numerous studies have looked at caspase and free radical formation inhibition during stresses including freezing, no studies have been reported looking to the effect of post-processing manipulation.

Figure 9:
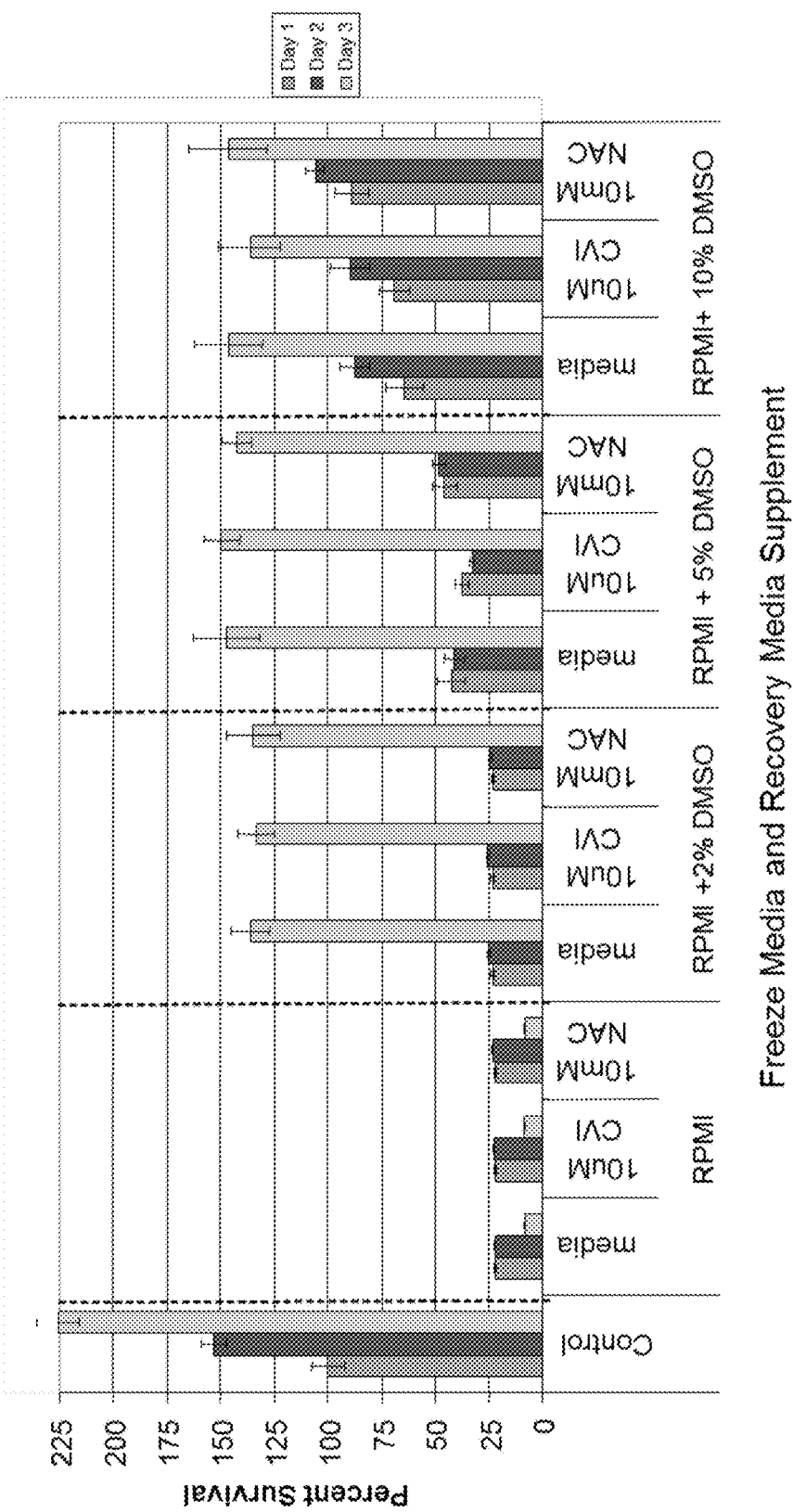
FIG. 9 compares C3A cell growth following post-freeze stress with caspase inhibitor (CVI) or oxidative stress modulator (NAC) supplements.

As such, in FIG. 9, C3A samples were frozen using industry standard protocols in culture media+0%, 2%, 5%, and 10% DMSO. Samples were then processed to remove the DMSO and placed into culture in standard media of media supplemented with a caspase inhibitor (CVI) or N-Acetyl-Cysteine (NAC) for the first 24 hours of post-processing culture. Culture media supplementation with CVI had little positive effect on cell recovery under any of the conditions evaluated. Utilization of the NAC additive to media yielded a positive effect on cell retention post-freeze in the 10% DMSO condition, and yielded an overall ~20% increase in sample recovery. Analysis of extended post-stress culture revealed that culture media supplementation with CVI or NAC had no downstream negative effect on cell division. This outcome supports the potential use of cell-guard additives to cell culture/media as no negative effect on the cells was observed during normothermic culture.

Figure 10A:
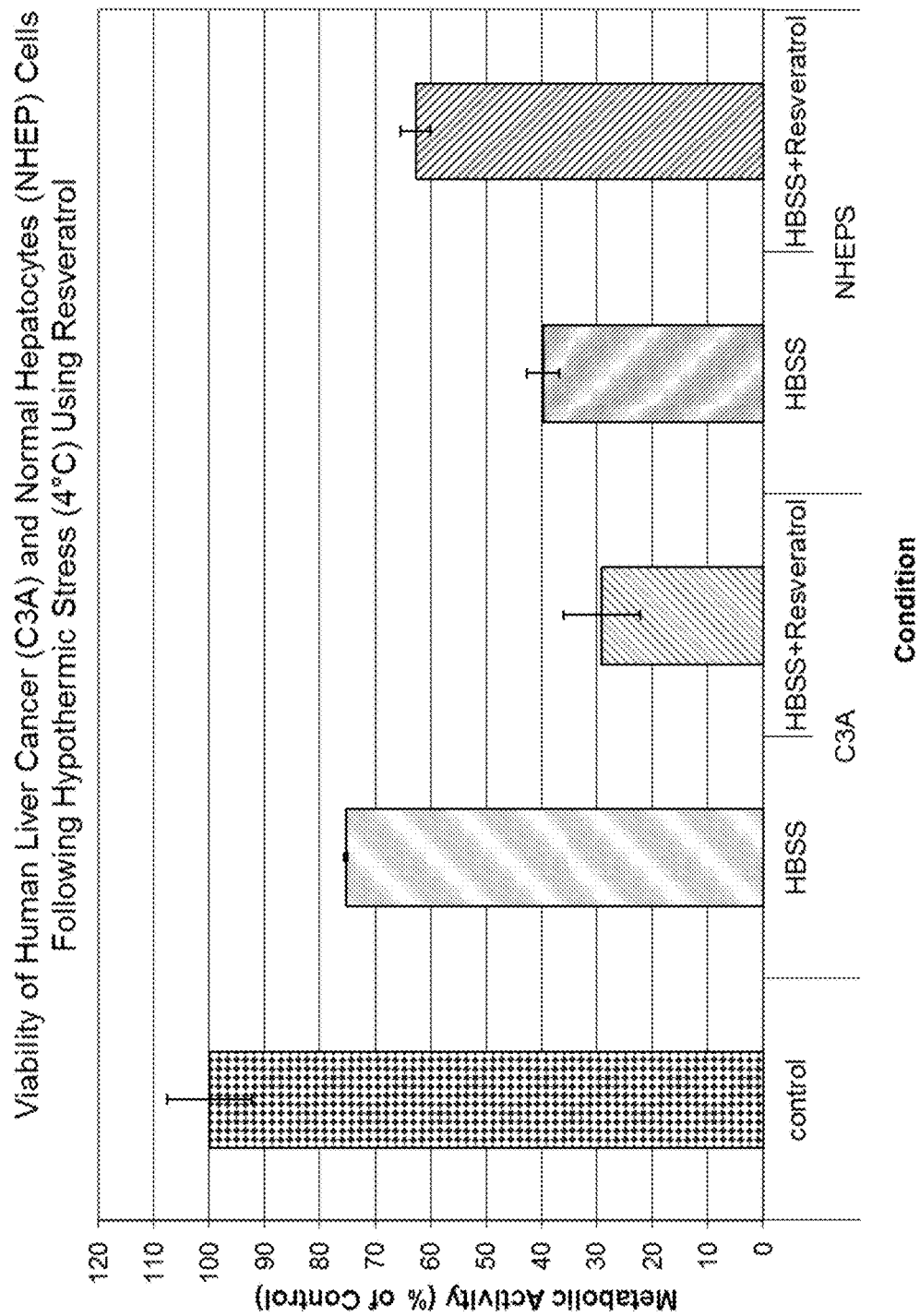

As described, the cell-guard technology has application across a broad base of cell systems and stress regimes. As shown in FIG. 10, the cell-guard supplements were tested in two human liver cell systems, hepatocytes and liver cancer cells (C3A), under a hypoxic normothermic stress model and a hypothermic stress model. While using resveratrol as the cell-guard supplement under hypothermic conditions, cell viability on hepatocytes was extended, but not on the C3A cells. The opposite was true when salubrinal was utilized during hypothermic stress on the cells; salubrinal extended cell viability for C3A cells, but not for hepatocytes. See FIG. 10: FIGS. 10A & 10B.

The reverse holds true when a normothermic stress regime is utilized (See FIG. 10: FIGS. 10C & 10D). Resveratrol extended the cell viability for C3A cells, but not for hepatocytes. Salubrinal extended the cell viability of hepatocytes, but not for C3A cells. The data in FIGS. 10C and 10D show that through normothermic stress pathway modulation using salubrinal or resveratrol, improved tolerance of the cells is observed.

Thus, the unfolded protein response (UPR) has been activated in response to stress in human hepatocytes since salubrinal, a UPR inhibitor, improves cellular response to thermal stress. In addition, modulation of the antioxidant and UPR pathways has been shown to improve tolerance of hepatocytes to normothermic hypoxic conditions. The table of FIG. 10 clarifies the experiments where hepatoma cell line, C3A, was exposed to hypothermic and normothermic stress regimes in a variety of carrier media supplemented with either salubrinal or resveratrol. These studies revealed that the UPR inhibitor, salubrinal, but not resveratrol, was able to protect cells from hypothermia-induced cell death. Application of the stress modulation model to normal rat hepatocytes (not shown) revealed that salubrinal failed to protect the cells where resveratrol was able to protect cells. This represented an exact opposite effect as seen in the cancerous C3A cells.

Given this unexpected finding, analysis was expanded to normal human hepatocytes subjected to the same thermal stress paradigm. Again, in contrast to C3A cells, resveratrol (FR-48), but not salubrinal, was able to completely maintain primary human hepatocytes subjected to thermal stress. Studies were conducted using a normothermic hypoxic stress model yielded similar yet opposite findings. In this regard, under normothermic hypoxic conditions, salubrinal was able to maintain normal hepatocytes but not resveratrol whereas for the cancerous C3A cells resveratrol but not salubrinal was effective (See FIGS. 10C & 10D).

These findings demonstrate that a switch of the stress regime from cold to hypoxic stress resulted in a flipping of results between cell types and reagents. A summary of the results are presented in the table of FIG. 10.

Interestingly, when the same stress manipulation paradigm was applied in the hypothermic stress regime using the organ transplant solution Viaspan, no positive selection was noted between the various cells. For instance, Viaspan is a preservation solution designed to transiently hold tissues at low temperatures, not to maintain or improve the native state of cells, tissues or organs. In fact, the formulation of known hypothermic storage solutions (as designed), including Viaspan, is toxic to cells under normothermic (37° C.) conditions.

One embodiment of the present invention addresses the need for tissues and organs to be protected from ischemic damage during donation, processing and transplantation, all of which typically occur at normothermic (ambient to 37° C.) temperatures. In another embodiment, organ viability and function can be maintained in a native state in order to provide for the highest probability of downstream engraftment and procedural success.

One challenge faced by the transplant community is how to best protect the tissue viability and function at the point of origin. A major focus of this effort has been to develop hypothermic shipping solutions. As such, a variety of hypothermic shipping solutions such as UW Solution (ViaSpan), HTK and Polysol have been developed over that past two decades and are used to ship various organs destined for transplant. While hypothermic storage has been effective to a degree none of these solutions are designed to mitigate normothermic stress experienced by all tissue during removal, processing, and implantation. Specifically, the various formulations, such as ViaSpan, are designed to mitigate cell response to extended cold storage. In fact, if these storage media were applied in processes carried out at normothermic temperatures they would be highly lethal. As such these strategies, components, and formulas are ineffective and not applicable to normothermic conditions.

As such, embodiments of the invention take into account the development of a "preconditioning medium" to (1) modulate the activation of stress pathways activated as a consequence of organ isolation and (2) ameliorate these stress pathways activated in tissues in response to the various stressors experienced during isolation, transport, and implantation. Cell-guard addresses the challenge in serving as a precondition reagent affording protection to cells, tissues and organs at the point of donation under normothermic conditions prior to downstream utilization such as in transplantation or storage.

In conclusion, the data suggest that cancerous (C3A) and normal (rat and human) hepatic cells respond to thermal and oxidative stress very differently and the modulation of these cell stress pathways can be used as a cell selection paradigm.

Human Corneal Endothelial Cells (HCECs)

Figure 11:
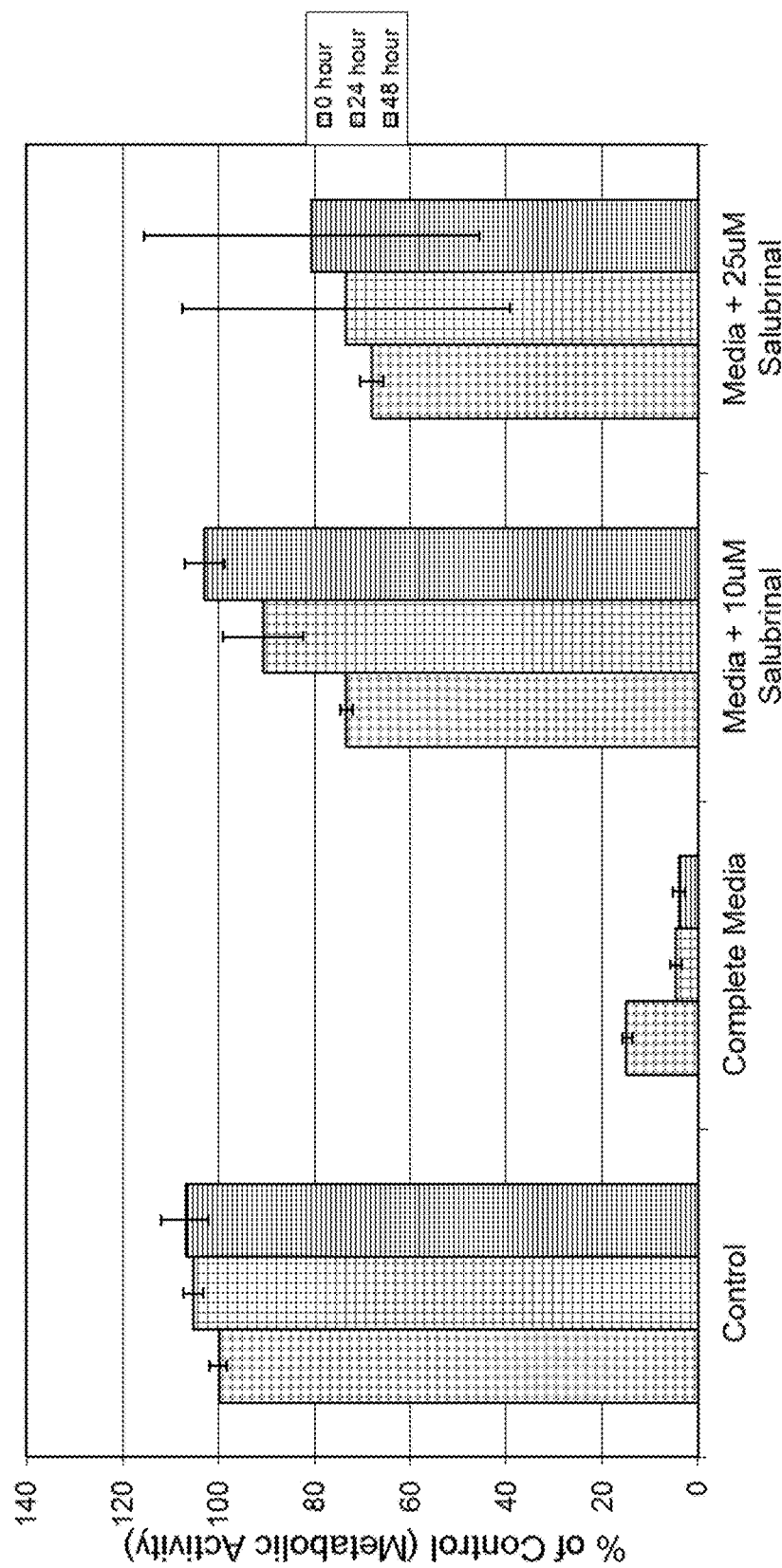
FIG. 11 illustrates the viability of HCECs following 18 hours of hypothermic storage at 6° C.

Human corneal endothelial cells (HCECs) have become increasingly important for a range of eye disease treatment therapies. Accordingly, a more detailed understanding of the processing associated stresses experienced by corneal cells may contribute to improved therapeutic outcomes. To this end, the unfolded protein response (UPR) pathway was investigated as a potential mediator of corneal cell death in response to cold exposure. FIG. 11 demonstrates that inhibiting the UPR pathway with salubrinal improves human corneal endothelial cell (HCEC) tolerance to stress.

Once cold stress-induced failure had begun in HCECs held at 4° C., necrosis accounted for the majority of cell death but with significant apoptotic involvement, peaking at several hours post-storage (4-8 hours). Western blot analysis demonstrated changes associated with apoptotic activation (caspase 9, caspase 3, and PARP cleavage). Further, the activation of the UPR pathway was observed through increased and sustained levels of ER folding and chaperone proteins (BiP, PDI, and ERO1-Lα) in samples experiencing significant cell death. Given the increase in immunostaining of BiP, a signature UPR protein, cells treated with the UPR inhibitor, salubrinal, and subjected to stress demonstrated that salubrinal exerted a protective maintenance effect during cold exposure. Modulation of the UPR pathway using the specific inhibitor, salubrinal, resulted in a 2-fold increase in cell survival in samples experiencing profound cold-induced failure. Furthermore, this increased cell survival was associated with increased membrane integrity, cell attachment, and decreased necrotic cell death populations.

As exemplified, data show that cells subjected to stress can activate at least four distinct cell stress pathways: caspase, AKT, MPTP, and UPR. When individually modulated, human cell retention, viability and function are improved. The synthetic supplements (e.g. salubrinal and apoptosis inhibitors) and natural compounds (resveratrol and Vitamin $D_3$) protect stress pathways in cells subjected to stress.

Conversely, addition of the UPR inducer, tunicamycin, during cold exposure resulted in a significant decrease in HCEC survival during the recovery period. These data implicate for the first time that this novel cell stress pathway may be activated in cells as a result of the complex stresses associated with thermal stress exposure. The data suggest that the targeted control of the UPR pathway during processing protocols may improve cell survival and function of HCEC, thus improving the clinical utility of these cells as well as whole tissues and organs (e.g. human corneas).

A molecular based cell death response, apoptosis, is initiated in cells in response to thermal stress. Studies have shown that changes associated with cold exposure, such as decreased membrane fluidity, pH change, osmotic imbalances, mitochondrial permeability transition pore opening, and oxidative stress can trigger a cell death response in a number of different cell systems. Furthermore, studies have demonstrated the beneficial effects of targeting these cold-induced molecular responses through solution formulation changes as well as the addition of specific chemical modulators (i.e. anti-oxidants, protease inhibitors, ion chelators.

The unfolded protein response (UPR) is the process in which a cell responds to the accumulation of misfolded proteins in the endoplasmic reticulum (ER). The UPR pathway has several functions, including correction of this accumulation through inhibiting translation of new proteins and up-regulating ER chaperone and folding proteins in an effort to clear the ER of these proteins. Another function of the UPR pathway is to initiate an apoptotic response if the ER stress remains too severe or prolonged. The UPR pathway, while identified relatively recently in human cell systems, has become a major area of study with various reports detailing its involvement in response to various cellular stress events. ER stress and subsequent UPR activation has been implicated in response to disease states, chemical exposure, cancer proliferation, aging, cell death, inflammation, autophagy, among others.

Studies suggest that the UPR may be a central pathogenic pathway with its activation triggering endothelial cell apoptosis through a mitochondrial based, caspase 9 mediated response. However, review of the previous investigations questioned whether this pathway is activated in response to complex changes and stresses associated with cold exposure. To this end, the role of the UPR has been investigated to determine its potential involvement in cellular demise associated with thermal stress exposure regimes.

Methods and Materials

Cell Culture: Various cells were obtained from commercial sources and maintained under standard culture conditions (37° C., 5% $CO_2$/95% air) in their respective culture media supplemented with 8% Fetal Bovine Serum (Atlanta Biologicals, Lawrenceville, Ga.), and other agents as appropriate including bovine pulmonary extract (Biomedical Technology Inc., Stoughton, Mass.), gentamicin sulfate (Invitrogen, Carlsbad, Calif.), epidermal growth factor (Millipore, Billerica, Mass.), nerve growth factor (Biomedical Technology Inc.), Anti-biotic/mycotic (Sigma-Aldrich, St. Louis, Mo.), ascorbic acid (Sigma-Aldrich), calcium chloride (Sigma-Aldrich), and chondroitin sulfate (Sigma-Aldrich). Cells were propagated in Falcon T-75 flasks and media was replenished every two days of cell culture.

Storage Media: Four different storage media were utilized for storage: complete growth media (CGM), Hank's Balance Salt Solution with calcium and magnesium (HBSS) (Mediatech, Inc., Manassas, Va.), ViaSpan (commercially available University of Wisconsin solution), and OptiSol (commercial whole cornea storage solution) (Bausch and Lomb, Rochester, N.Y.).

Thermal Stress Regime: Cells were seeded into 96-well tissue culture plates (13,000 cells per well) and cultured for 24 hours into a monolayer. Culture media was decanted from experimental plates and replaced with 100 µl/well of the pre-cooled (4° C.) solution (complete growth media, HBSS with calcium and magnesium, ViaSpan, or OptiSol). Cultures were maintained at 4° C. for 18 hours to 9 days. Following cold storage, the media were decanted, replaced with 100 µl/well of room temperature (~25° C.) complete culture media and then placed into standard culture conditions (37° C., 5% $CO_2$) for recovery and assessment.

Cell Viability Assay: To assess cell viability the metabolic activity assay, alamarBlue™ (Invitrogen) was utilized. Cell culture medium was decanted from the 96-well plates and 100 µl/well of the working alamarBlue™ solution (1:20 dilution in HBSS) was applied. Samples were then incubated for 60 minutes (±1 min) at 37° C. in the dark. The fluorescence levels were analyzed using a Tecan SPECTRA-FluorPlus plate reader (TECAN, Austria GmbH). Relative fluorescence units were converted to a percentage compared to normothermic controls set at 100%. Readings were taken immediately following removal from hypothermic storage as well as 24 and 48 hours of recovery.

Chemical Additions: Modulation of the UPR was accomplished through the use of salubrinal (UPR-specific inhibitor), tunicamycin (UPR-specific inducer), resveratrol, AKT, Vitamin $D_3$, caspase and MPTP inhibitors, among others. For instance, salubrinal (EMD Chemicals Inc., Gibbstown, N.J.) was added to media at working concentrations of 10 and 25 µM immediately before utilization. Tunicamycin (EMD Chemicals Inc.) was added to ViaSpan at a working concentration of 2 ug/mL immediately prior to use. All chemicals were diluted in water, ethanol, or DMSO prior to utilization and DMSO controls were conducted to ensure no effect of the dilution vehicle.

Fluorescence Microscopy: Samples in 96-well plates were assessed for the presence of live, necrotic or apoptotic cells through triple labeling using Hoechst [81 µM], propidium iodide [9 µM], and Y oPro-1 [0.8 µM] (Molecular Probes, Eugene, Oreg.), respectively. Probes were added to samples and incubated in the dark for 20 minutes prior to imaging. To assess membrane integrity a dual label of calcein-AM [4 µM] and propidium iodide [9 µM] was utilized. Dual label probes were added to the samples and incubated for 30 minutes in the dark. All fluorescence images of labeled cells were obtained at 1, 4, 8 and 24 hours post-storage using a Zeiss Axiovert 200 fluorescent microscope with the AxioVision 4 software (Zeiss, Germany).

Flow Cytometric Analysis: Counts of the unlabeled (live), necrotic (PI [1.5 µM]) and apoptotic (YOPRO-1 [0.1 µM]) labeled cells were obtained using microfluidic flow cytometry (Millipore). Probes were added to each sample and incubated in the dark for 20 minutes prior to cell collection. Counts of cells with polarized and depolarized mitochondria (JC-1 [7.7 µM]) were also obtained via microfluidic flow cytometry. Samples were labeled, collected and analyzed at 1, 4, 8 and 24 hours post-storage. Analysis was performed using the CytoSoft 5.2 software for the Guava PCA-96 system.

Western Blot Analysis: Cells were cultured in 60 mm Petri dishes to form a monolayer. Cell culture media was removed and replaced with 4 mL of pre-cooled (4° C.) solution and dishes were placed at 4° C. for 18 hours. Following stressed exposure, solutions were decanted and replaced with 4 mL of room temperature culture media and placed into standard culture conditions (37° C., 5% $CO_2$) for recovery. Cell lysates were collected 1, 4, 8 and 24 hours post-storage using ice-cold radio-immunoprecipitation assay cell lysis buffer with protease inhibitors. Samples were homogenized by vortex mixing and centrifuged at 15,000 rpm for 15 minutes at 4° C. Protein concentrations were quantified using the bicinchonic acid protein assay (Thermo Fisher Scientific, Rockford, Ill.) and a Tecan SPECTRA FluorPlus plate reader. Equal amounts of protein (30 µg) for each sample were loaded and separated on a 10% SDS-PAGE gel (Bio-Rad, Hercules, Calif.). Proteins were transferred to PVDF membranes (Bio-Rad) and blocked with a 1:1 mixture of NAP™-Blocker (G-Biosciences, Maryland Heights, Mo.) with 0.05% Tween-20 in PBS for 2 hours at room temperature. Membranes were incubated at 4° C. overnight in the presence of each antibody: anti-human caspase 9, anti-human caspase 3, anti-human PARP, anti-human Bip, anti-human calnexin, anti-human ERO1-Lα, anti-human PDI and anti-human β-Tubulin (Cell Signaling Technology, Danvers, Mass.). Membranes were then washed three times with 0.05% Tween-20 in PBS and exposed with horseradish peroxidase-conjugated secondary antibodies for 1 hour at room temperature. Membranes were again washed three times with 0.05% Tween-20 in PBS before detection with the LumiGLO®/Peroxide chemiluminescent detection system (Cell Signaling Technology). Membranes were visualized using a Fujifilm LAS-3000 luminescent image analyzer. Equal protein loading was achieved through initial quantification of all samples and confirmed by Ponceau S staining of PVDF membranes prior to blocking as well as probing for β-Tubulin levels.

Data Analysis: Viability experiments were repeated a minimum of three times with an intra-experiment repeat of seven replicates. Western blots, flow cytometry and fluorescence microscopy were all conducted on a minimum of three separate experiments. Standard errors were calculated for viability values and single-factor "ANalysis Of VAriance" (ANOVA) was utilized to determine statistical significance.

Results

Effect of Hypothermic Exposure on Human Corneal Endothelial Cell Survival

HCECs displayed a variable level of cold sensitivity in vitro that was dependent upon the media and duration of hypothermic storage as shown in FIG. 12. This was characterized by a decrease in viability immediately following 18 hours of cold storage in all solutions utilized: CGM, HBSS, ViaSpan and OptiSol. Storage in CGM resulted in 14.9% (±3.8) viability, while samples stored in OptiSol retained 57.4% (±6.5) viability and storage in HBSS and ViaSpan yielded retention of 99.0% (±8.2) and 91.5% (±4.0) viability, respectively. Despite the levels of cell death observed, samples were able to recover and repopulate in culture following 18 hours of cold exposure regardless of the media utilized.

As the storage interval was increased, however, corresponding decreases in sample viability were evident across all conditions (FIG. 12). Following 24 hours of cold exposure samples stored in CGM yielded few remaining viable cells (3.9% (±1.0)) and no replicative capacity. HCECs stored in OptiSol demonstrated a marked decrease in viability, compared to 18 hour exposure, retaining only 29.3% (±8.9) metabolic activity and an inability to repopulate to normothermic control levels by 48 hours post-storage. Storage in HBSS and ViaSpan demonstrated lower reductions in viability retaining 85.8% (±9.9) and 86.8% (±6.1) respectively, immediately following 24 hour exposure. Further increasing the cold exposure interval to two days resulted in more pronounced cell loss with a complete loss of viability in the CGM and OptiSol stored HCEC samples. HBSS samples decreased to 4.9% (±1.5) viability while the ViaSpan samples retained a high level of metabolic activity (68.2% (±7.7)) as well as an ability to repopulate to normothermic control levels during the recovery period (See FIG. 12).

Post-cold exposure sample viability data were confirmed via fluorescence microscopy probing for viable, necrotic and apoptotic cells using hoechst, propidium iodide (PI) and Yo-Pro-1, respectively. Micrographic assessment demonstrated a similar level of viable cells remained following the various hypothermic exposure intervals in the four solutions utilized as measured by alamarBlue (data not shown). These analyses also allowed for the assessment of the modes of cell death contributing to sample demise following hypothermic storage of HCECs. Fluorescence microscopy revealed that the primary mode of cell death involved in HCEC preservation-induced cellular demise was necrosis as indicated by the high incidence of PI-labeled (red) cells. Along with necrosis it was noted that a considerable amount of apoptotic cells (green) were detected throughout the 24 hours post-storage, with a peak occurrence of this population at 4-8 hours following removal from the cold. These data were consistent with studies on other cells systems following cold exposure, where a delayed apoptotic peak and large necrotic population have been reported.

Activation of Apoptosis Following Hypothermic Exposure

Following the establishment of viability profiles for HCECs stored for various intervals coupled with the observation of a molecular-based component to cell death, western blot analysis was conducted in an effort to decipher the activation of specific cold-induced cell stress pathways. Samples were collected after 1, 4, 8 and 24 hours of recovery following 18 hours of cold storage in either CGM, HBSS (Hank's Balanced Salt Solution), ViaSpan or OptiSol and total protein was extracted. The assessment of proteins associated with apoptotic activation revealed a correlation between the loss of viability and activation of the apoptotic cascade (FIG. 13A).

Figure 13A:
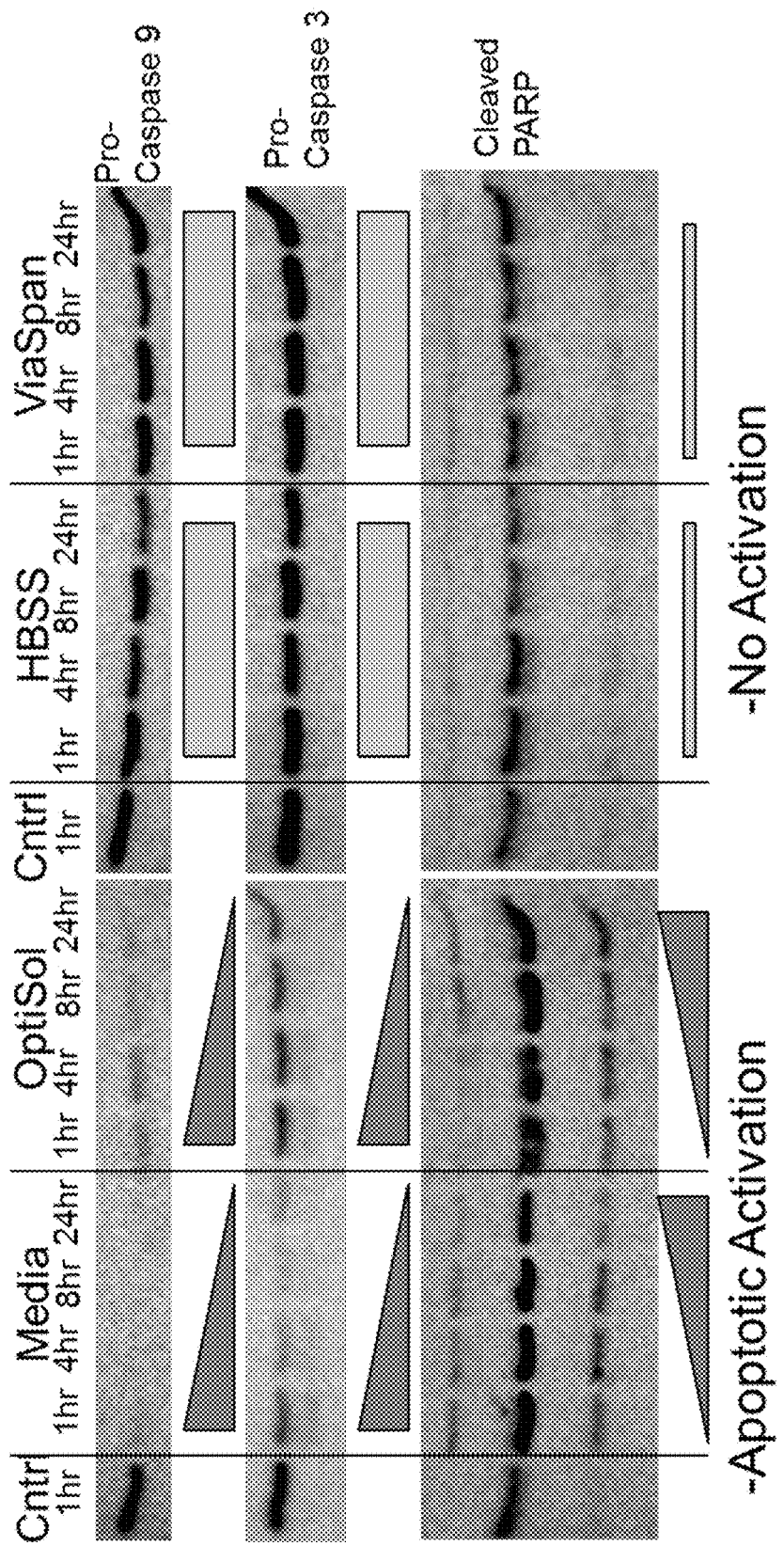
FIG. 13A depicts apoptotic activation of proteins via a temporal Western blot analysis of HCECs following 18 hours of hypothermic exposure.

In FIG. 13A, targeted assessment of caspase 9, a specific mediator of mitochondrial (intrinsic) based apoptotic activation, revealed cleavage (activation) of the pro-form intermediate at 1 hour post-storage in the CGM stored samples (21.5% as compared to control levels) with a subsequent complete loss (2.5%) by 24 hours post-exposure while OptiSol storage demonstrated a reduction in pro-caspase 9 without a complete loss throughout the time course (19.2% at 24 hours of recovery). Pro-caspase 9 levels in HBSS and ViaSpan stored HCECs maintained higher and more consistent levels throughout the initial 24 hours post-cold exposure recovery period (~60-70% as compared to controls). This maintenance in pro-caspase 9 levels was consistent with the elevated viability levels observed under these conditions.

Assessment of the downstream apoptotic mediator, caspase 3 (See FIG. 13A), revealed a similar pattern of cleavage as observed with pro-caspase 9. Decreases in pro-caspase 3 levels were detected in both the CGM and OptiSol stored HCECs (13.2% and 42.3% at 24 hours post-storage, respectively), with more pronounced cleavage noted in the CGM samples and to a lesser extent in OptiSol storage as compared to normothermic control levels. As with caspase 9, caspase 3 activation correlated with the viability data. Likewise, HBSS and ViaSpan stored cells demonstrated a pattern of sustained pro-caspase 3 levels throughout the post-storage time course indicating a lower level of apoptotic activity and overall cell death. With the observed caspase 3 activation, assessment of the active caspase 3 target, Poly (ADP-ribose) polymerase (PARP), was conducted to further support the evidence of apoptotic signal progression following cold storage (FIG. 13A). PARP is a DNA repair enzyme whose cleavage is indicative of late stage apoptosis and cells' commitment to completing cell death. Western blots revealed an increase in PARP cleavage in the CGM and OptiSol samples as compared to the HBSS and ViaSpan samples and normothermic controls. Examination of PARP cleavage revealed a similar pattern of apoptotic activation in the CGM and OptiSol samples with noticeably less activation in the HBSS and ViaSpan samples. These data further confirmed apoptotic activation in HCECs leading to preservation-induced viability loss.

Involvement of the Unfolded Protein Response Following Cold Exposure

Figure 13B:
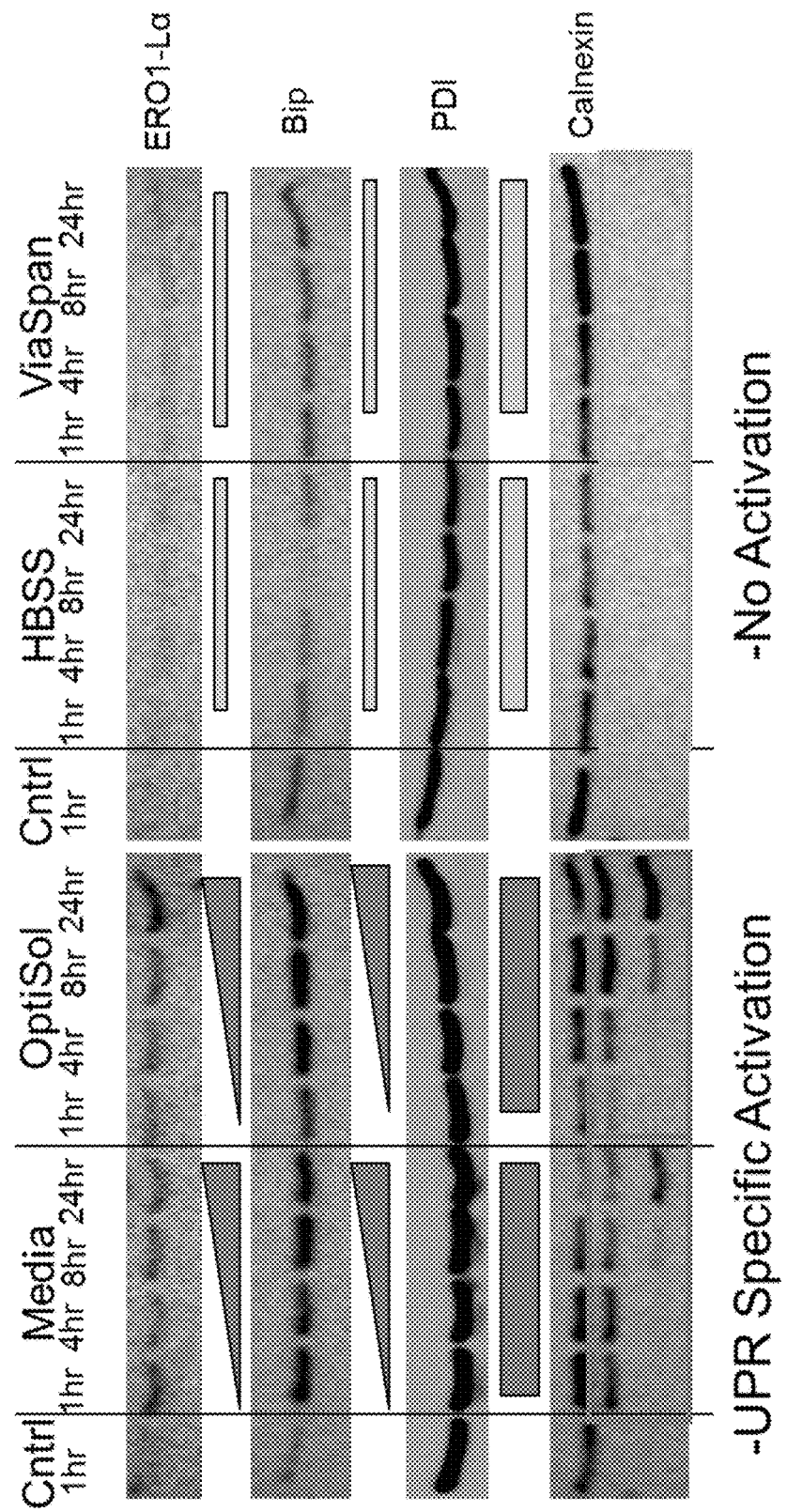
FIG. 13B depicts UPR specific activation via a temporal Western blot analysis of HCECs following 18 hours of hypothermic storage.

Following the identification of apoptosis through both fluorescence microscopy and western blot analysis, an investigation of the involvement of ER stress and the UPR pathway in response to hypothermic exposure was conducted. In FIG. 13B, Western blots were performed examining the levels of ER folding and chaperone proteins, including BiP, ERO1-Lα, PDI and calnexin, in HCEC isolates at 1, 4, 8 and 24 hours recovery post 18 hours cold storage. Similar to apoptotic-associated protein changes, a correlation was noted between a loss of sample viability and changes in the ER stress protein levels and the subsequent UPR activation. In the CGM and OptiSol samples, increases in BiP and ERO1-Lα were observed as compared to normothermic controls (FIG. 13B). A time dependent increase in BiP was seen in CGM and OptiSol stored samples as both peaked at 24 hours post-storage (359.7% and 455.8%, respectively). Analysis of ERO1-Lα levels demonstrated an immediate peak 1 hour post-exposure for CGM samples (123.0%) and a delayed peak for OptiSol samples (172.9% at 24 hours of recovery). Comparatively, HBSS and ViaSpan stored samples demonstrated lower overall levels of these proteins with no time dependent up-regulation. Examination of PDI revealed that levels remained relatively consistent throughout the initial 24 hours following hypothermic exposure for all conditions tested. Probing for calnexin also revealed a time related cleavage in CGM and OptiSol samples, an event reported in response to apoptotic stimuli. Conversely, HBSS and ViaSpan samples exhibited no calnexin cleavage throughout the 24 hour recovery interval. These data suggest that changes in proteins associated with ER stress and UPR activation occur in a manner that correlates with the activation of the apoptotic cascade in response to cold exposure.

Figure 14A:
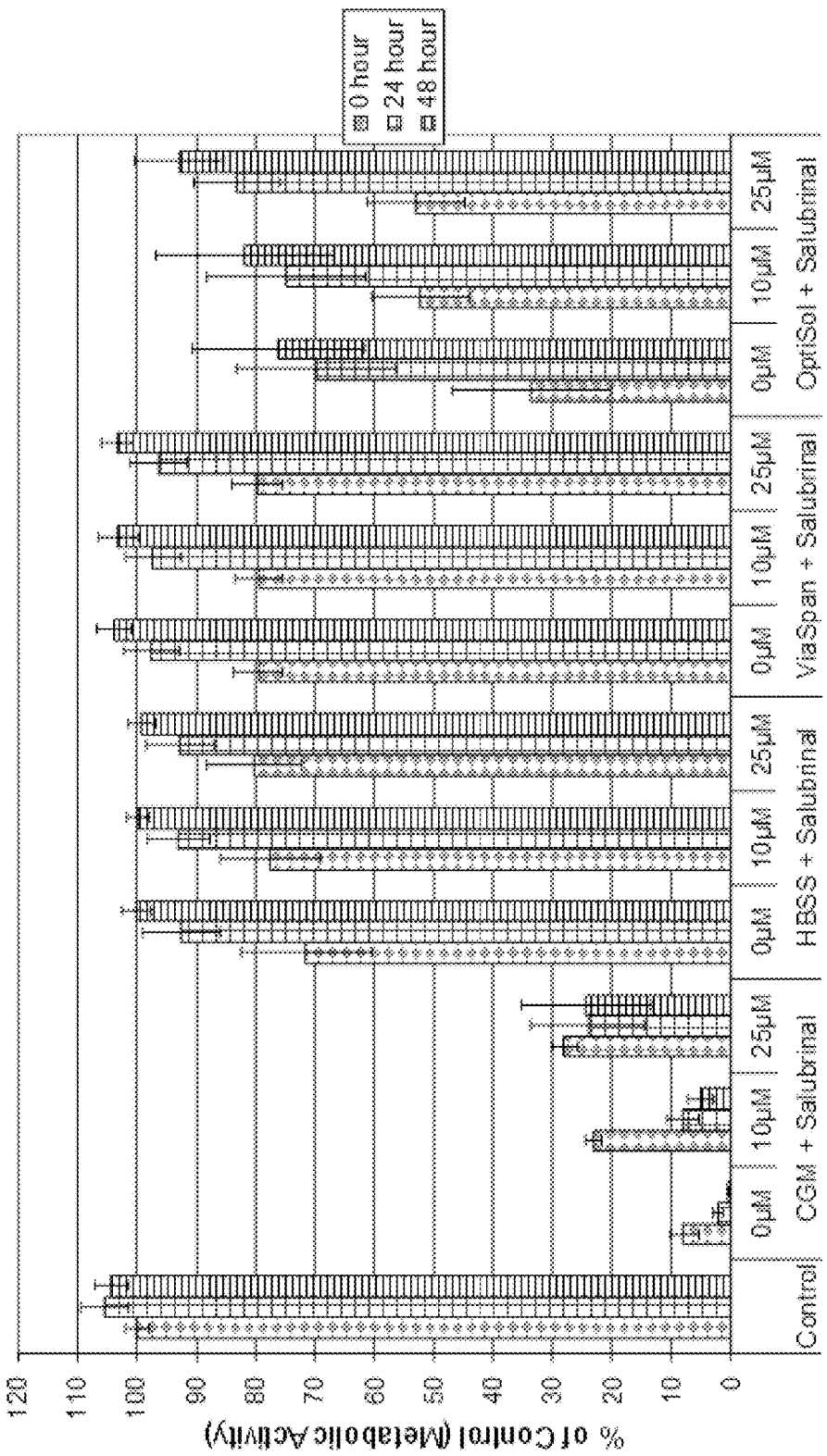
FIG. 14A illustrates the viability of HCECs following 24 hours of hypothermic storage at 4° C. with the addition of a salubrinal supplement.
Figure 14B:
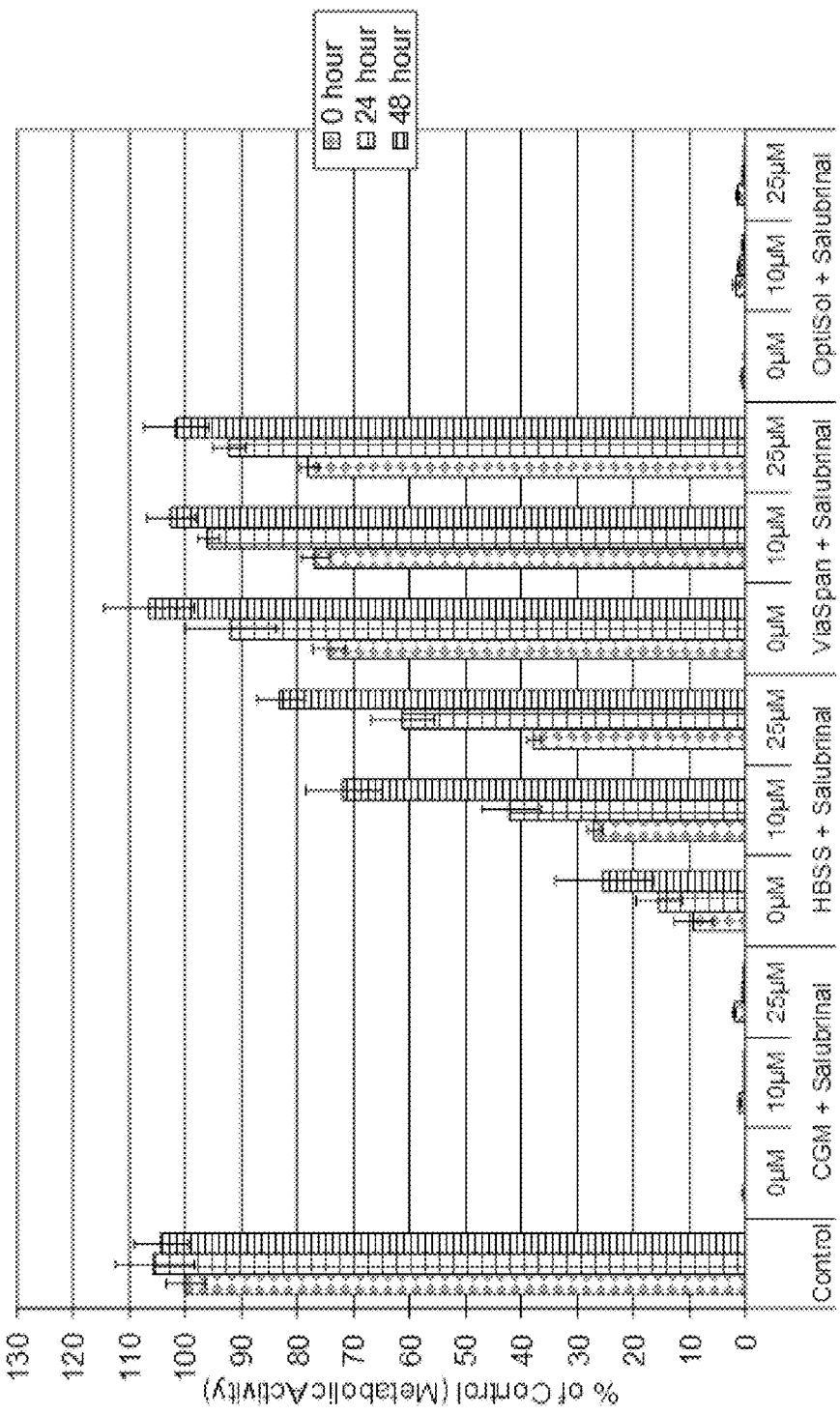
FIG. 14B illustrates the viability of HCECs following 48 hours of hypothermic stress at 4° C. with the addition of a salubrinal supplement.
Figure 14C:
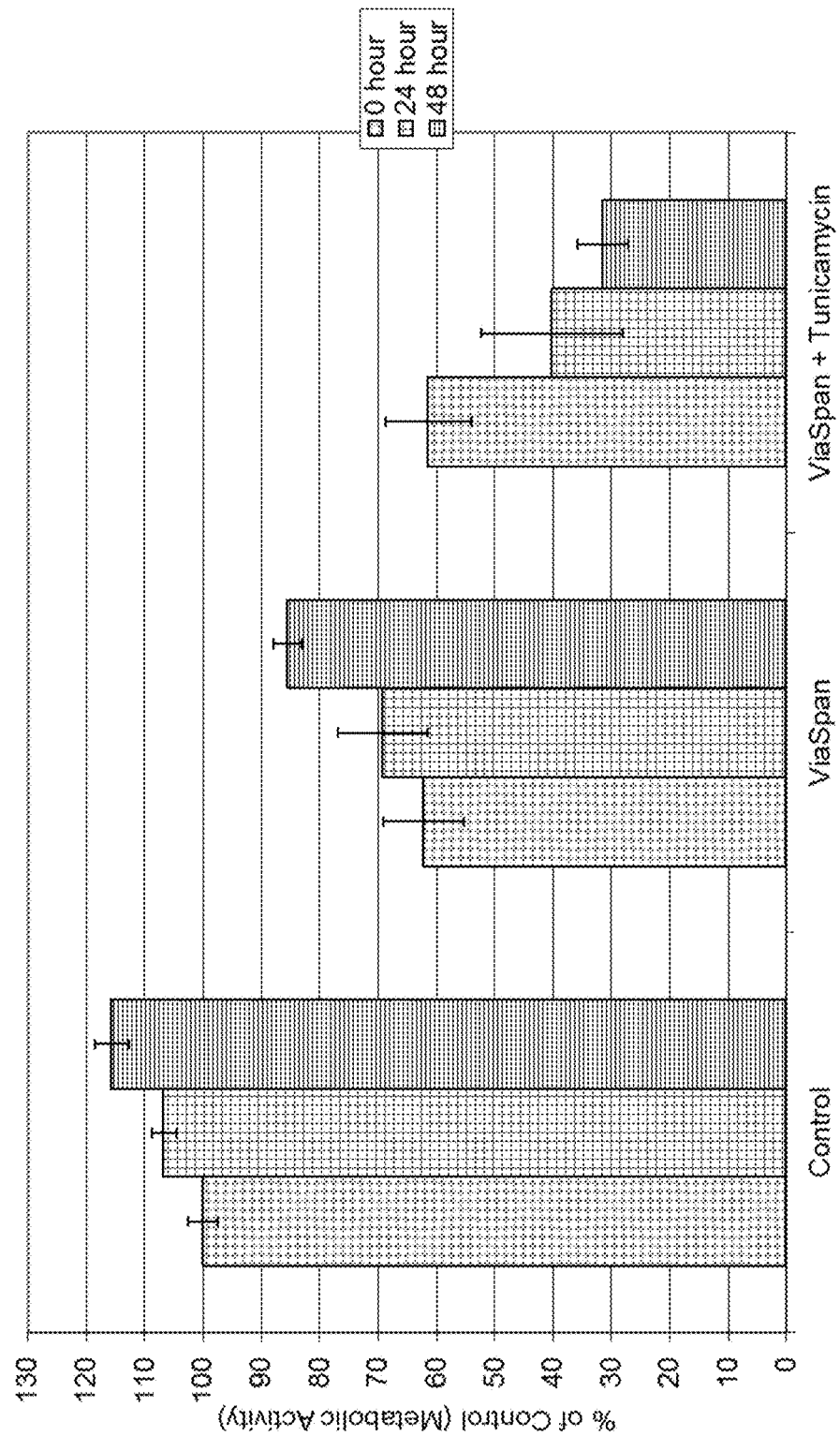
FIG. 14C depicts the viability of HCECs following 3 days of hypothermic storage with tunicamycin.

Effect of UPR Specific Chemical Modulation on Human Corneal Endothelial Cell Survival Identification of ER stress and UPR involvement in HCEC response to cold exposure led to investigating the effect of targeted, specific modulation of the UPR pathway as shown in FIGS. 14A, 14B, 14C. UPR inhibition and UPR induction studies were conducted through the addition of salubrinal (inhibition) and tunicamycin (induction) during hypothermic storage to confirm the role of the UPR pathway in cold-induced cell death. (NOTE: The asterisks, **, highlight differences to illustrate the beneficial effects of cellguard additives, or sell supplements.)

To examine the effect of UPR specific inhibition, HCECs were stored at 4° C. in the presence of salubrinal for 18 hours, 24 hours and 2 days, allowed to recover and sample viability assessed (FIG. 14A). Cold storage for 24 hours in the presence of salubrinal resulted in a pattern of improved HCEC survival during the 48 hours recovery period (FIG. 14A). HBSS and ViaSpan samples remained highly viable (70-80%) and demonstrated no differences with salubrinal addition at this storage interval (p=0.28 and p=0.98, respectively). CGM and OptiSol stored HCECs demonstrated considerable improvements following salubrinal addition as these systems began to undergo hypothermic stress dependent failure. Storage in CGM alone resulted in 7.9% (±2.4) viability immediately following storage with a subsequent decrease during recovery resulting in complete loss of viability. Addition of 10 µM and 25 µM salubrinal, however, yielded improved post-storage viabilities of 23.1% (±1.4) and 28.0% (±2.1), respectively (p<0.001). Interestingly, the 25 µM condition allowed for the subsequent maintenance of HCECs as viability was retained over the 48 hour recovery period. Similarly, HCEC storage in OptiSol with and without salubrinal addition for 24 hours resulted in similar patterns as the aforementioned CGM storage with post storage viabilities of 33.5% (±13.3), 52.3% (±8.2) and 53.9% (±8.2) (OptiSol with 0 µM, 10 µM and 25 µM salubrinal, respectively) (p<0.01). These UPR inhibition data demonstrated a concentration dependent increase in HCEC viability that translated to improved survival throughout the 48 hour recovery period.

An extension of the hypothermic exposure interval from 1 to 2 days provided additional verification of the involvement of UPR and beneficial effect of its inhibition (FIG. 14B). Following 2 days of cold storage, a complete loss in viability in all CGM and OptiSol HCECs samples was observed. Interestingly, following this storage interval, HBSS samples succumbed to preservation-induced cell death yielding sample viability of 9.3% (±3.5) immediately post-storage. Inclusion of salubrinal during cold storage provided dose-dependent increases in overall viability to 26.9% (±1.5) and 37.8% (±1.4) (10 µM and 25 µM, respectively) (p<0.001). As with the 24 hour sample, 48 hour storage in ViaSpan yielded minimal cell loss and no effect of salubrinal supplementation (74.3% vs. 76.7%, p=0.87). These data suggest that UPR specific inhibition has a beneficial effect only once HCECs begin to demonstrate substantial losses in viability (greater than 50%).

To further test UPR involvement, induction studies were conducted to determine whether UPR activation would have a negative effect on HCEC survival following hypothermic storage. In FIG. 14C, the UPR specific inductor, tunicamycin, was added to ViaSpan and HCEC samples were stored at 4° C. for 3 days in the presence and absence of tunicamycin then assayed for viability at 0, 24 and 48 hours of recovery. Tunicamycin addition had no immediate effect on post-storage viability as both storage conditions yielded ~60% cell survival (p=0.86). However, significant differences in the storage conditions became evident as assessment continued through the recovery period. Following 24 hours of recovery a survival difference of 29.0% was noted between the conditions. This differential further increased to 53.9% by 48 hours post-storage (p<0.001). These findings further support the significant effect that the UPR pathway may play in cell survival following cold exposure.

Effect of UPR Specific Modulation on Cell Death Populations Following Cold Storage Following the observation of differences in viability through the targeted modulation of the UPR, we next analyzed what effect this targeted approach has on the level and timing of cell death following hypothermic storage. HCECs were held at 4° C. for 24 hours in various solutions (CGM, HBSS, ViaSpan and OptiSol) with and without the addition of 25 μM salubrinal and assessed via microfluidic flow cytometry and fluorescence microscopy. Analysis of the apoptotic and necrotic populations was conducted to examine the effect UPR inhibition (25 μM salubrinal) had on cell death populations post-storage. Temporal Yo-Pro-1/PI flow cytometric analysis revealed that necrosis accounted for a larger percentage of the total population in uninhibited samples as compared to their UPR inhibited counterpart. In this regard, the complete growth medium (CGM) and Opti-Sol stored cells demonstrated the largest differences in levels of necrosis (data not shown). Interestingly, examination of the apoptotic populations revealed the opposite trend, with the UPR inhibited samples having a larger apoptotic population than in uninhibited samples. This suggests that UPR inhibition may have resulted in an increased prevalence of cells that survive the initial stress of cold exposure but experienced sufficient damaging effects to trigger an apoptotic response following storage, thus resulting in increased populations of both apoptotic and viable cells as compared to uninhibited samples.

Figure 15A:
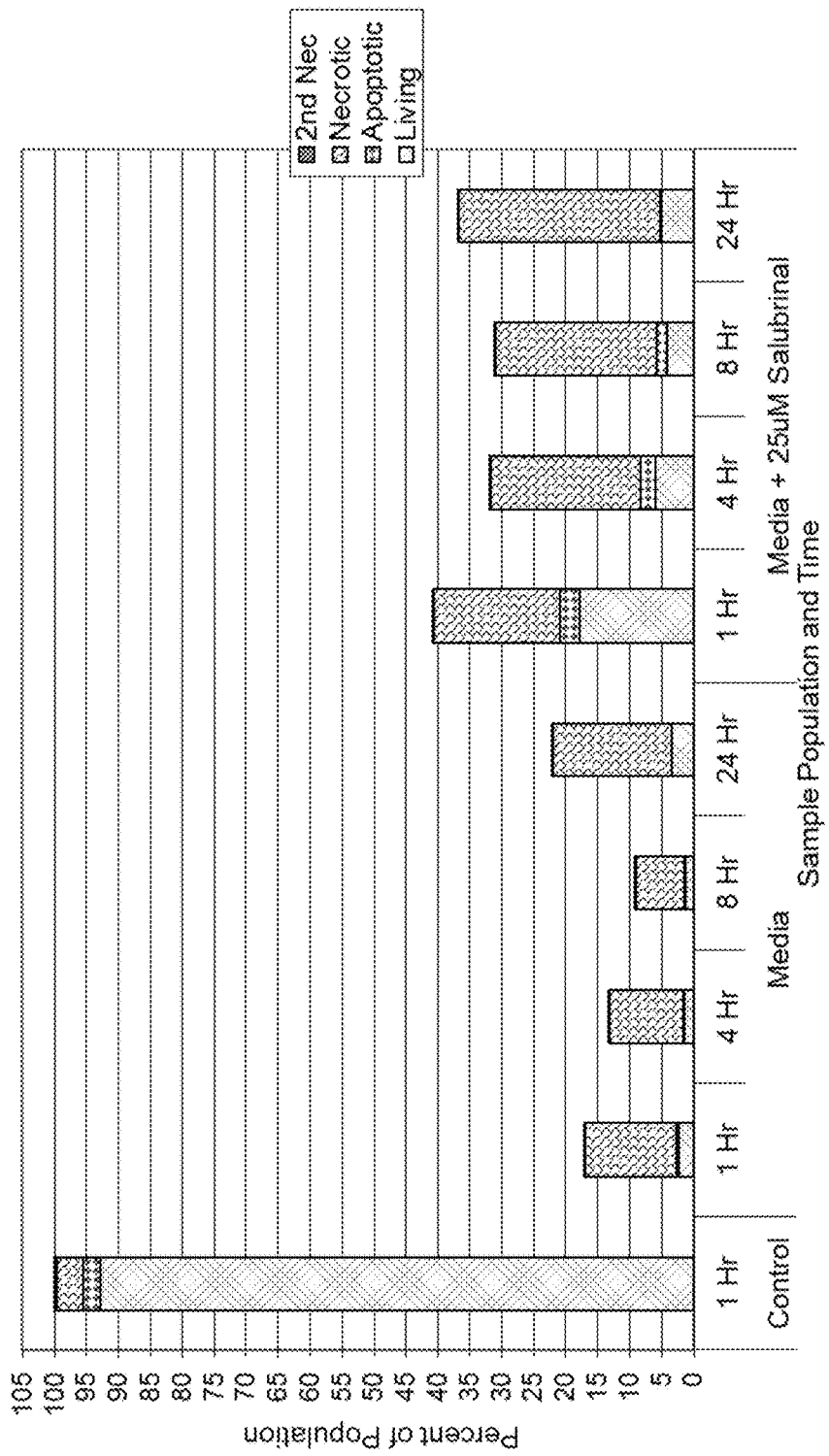
FIG. 15A is a temporal analysis of cell death in HCECs following 24 hours hypothermic storage using CGM.

As shown in FIGS. 15A & 15B, when samples were normalized to the normothermic control, it was observed that necrotic populations between UPR inhibited and uninhibited samples were similar. The levels of apoptosis, however, were elevated in the inhibited samples as compared to uninhibited conditions at each time point (FIGS. 15A and 15B). The most noticeable differences between the conditions were in the level of viable cells as well as the overall total cell retention (as noted by the total stacked population in both FIGS. 15A and 15B). This was particularly evident in the CGM and OptiSol HCEC samples. These data illustrate that UPR specific inhibition had a beneficial effect through an increased retention of total cells during hypothermic exposure resulting in an elevated viable cell population.

These data were corroborated visually via fluorescence microscopy utilizing tri-stain (Hoechst, PI, Yo-Pro-1) to examine the levels of viable, necrotic and apoptotic and a dual-staining (calcein-AM, PI) to examine membrane integrity (live and dead cells) between UPR inhibited and uninhibited samples (data not shown). Specifically, CGM storage for 24 hours with and without salubrinal yielded patterns similar to those observed with flow cytometry. Increases in viable cell populations and overall cell retention in UPR inhibited samples compared with uninhibited samples were found. Micrographs of calcein-AM and propidium iodide probed samples revealed that salubrinal addition resulted in a marked increase in both membrane integrity as well as cellular attachment during the recovery period. These data further support the beneficial effect that the specific targeting of the UPR pathway has on HCEC tolerance to hypothermic stress.

Discussion

In this study, the role of UPR activation in cellular demise was examined following cold exposure. In an effort to examine the universality of UPR involvement, four unique storage media were utilized, each of which represented a vastly different composition ranging from a balanced salt solution (HBSS) to complete growth media (CGM) to commercial cold storage media (OptiSol and ViaSpan). The motivation behind the selection of these diverse media was not to compare solution performance but to examine the activation, progression, and modulation of UPR based cell death associated in preservation failure regardless of storage time or base medium. Investigation of the differential level of survival after a given storage time due to basal medium formulation, while interesting, was beyond the scope of this study.

As it is progressively recognized that all cold storage media fail to protect cells as storage time increases, the "extended" intervals specific to each media in examining UPR involvement were examined. Assessment of HCECs revealed a contrast in cold sensitivity in vitro with viability dependent on exposure duration and solution. Cell death analysis demonstrated that necrosis was the dominate mode of cell death once failure had begun regardless of the media utilized. A sizeable population of apoptotic cells was also noted in the hours following storage, illustrating the involvement of a complex molecular-based response to lethal cold exposure. Furthermore, these cell death populations displayed a temporal response to the cold with a peak in apoptosis observed several hours (4-8) into recovery in addition to a continued increase in necrosis throughout the initial 24 hour recovery period. This illustrates the fact that physical stress alone is not the only factor responsible for cellular demise but instead cold-induced stress pathways are being activated in response to cold exposure.

Previous studies have reported on the involvement of caspases in response to cold stress as well as the beneficial effect of their inhibition. Western blot investigations demonstrated the involvement of caspases as well as the downstream target PARP in HCEC cold-induced cell death. In particular, this analysis suggested that the mitochondrial-mediated (intrinsic) pathway of apoptosis was being activated. This was an important observation as it led to investigation of UPR involvement, as reports have shown that the UPR mediates the activation of an apoptotic response, at least partially, through the mitochondria.

The examination of proteins specific to ER stress and the subsequent UPR activation confirmed that changes, such as the up-regulation of ER chaperones and protein folding proteins, were observed in correlation with increased losses in sample viability. This provided the first implication of the UPR pathway activation in response to severe cold stress in an in vitro cell model. While there has been an increasing focus on the UPR pathway in relation to other cell stressors (i.e. ischemia, oxidative stress, disease states), there was little to no evidence that the UPR is involved with hypothermic-induced cellular demise.

Further, investigation of UPR pathway involvement through its specific modulation provided supporting evidence of its role during cold exposure. Comparison between UPR inhibited and non-inhibited samples revealed that modulation of the UPR resulted in increased metabolic activity, membrane integrity, cellular attachment, and overall sample viability. Additionally, the specific induction of the UPR resulted in a pronounced increase in cell death throughout the recovery period as well as the accelerated activation of cold-induced cell death as compared to non-induced samples. These data provide additional evidence implicating the UPR's involvement as a cold-induced stress pathway playing a role in delayed cell death.

The data indicate a clear need for further in-depth studies on the UPR in response to cold exposure. This study was an important first step for human corneal endothelial applications given that many of these processes involve subjecting corneal tissue to cold prior to utilization. The in vitro model employed in this study led to studying this specific subset of corneal cells as HCECs have little to no replicative capacity; this is in contrast to using whole cornea from an animal, a model which contains endothelial cells that have the ability to divide and repopulate following endothelial death and damage.

The results obtained in this study on individual HCEC populations differed from the results of studies examining whole cornea storage in terms of the length of storage times achievable (i.e. 24 hours for HCEC storage in OptiSol vs. 7 or more days for whole cornea storage in OptiSol). The difference may be attributed to a number of factors that differ between a whole cornea and HCEC cell culture. The activation of the UPR was observed in all solutions tested at these "extended" storage times demonstrating that this pathway may serve as an important target particularly for cell-based therapies and potentially for future studies on whole cornea.

This study represents a step in linking UPR activation and HCEC storage failure; however, there is still a need for understanding the direct causal relationship. While the identification and modulation of caspases represents a fundamental advance, it does not account for the entire cold-induced cell death story. As such, there remains a definitive need for further stress pathway identification for improved control. The identification of novel cold stress pathways, such as the UPR, may allow for a more specific molecular control of cell responses to improve survival and function. This in turn may translate into improved outcomes for down-stream corneal utilizations (i.e. transplants, engineered tissues, etc.). In summary, the UPR appears to be an important pathway for future studies and holds potential for manipulation as technologies continue to more forward into more molecular based approaches.

Cell Selection Using Differential Stress Pathway Responses

Cell Selection Technique

Cell selection is a technique utilized throughout various aspects of cell and molecular biology. For instance, flow cytometry/fluorescence activated cell sorting (FACS) originally developed in 1969 is one exemplary tool in the modern research laboratory. The versatility of FACS is notable, yet a time consuming cell separation. Currently, FACS is being tested for its ability to detect cancer stem cells. Other separation systems [such as Dynabeads®] may be less stressful to cells, but still require centrifugation steps to purify different cell populations. Both are limited by the requirement that an antibody must be identified that can selectively adhere to the cells and have a high enough affinity/specificity to ensure that the cell sorting process is efficient. Yet cell sorting is critical to a number of research and clinical areas that include the future application of hESCs and iPSCs in stem cell therapy, regenerative medicine and drug discovery. This is especially true when one considers that nearly all reports to date state that these cells can cause teratomas in situ. Thus, it is desirable that new cell selection procedures be developed that can effectively eliminate select cell populations in a mixed (heterogenous) group of cells that, in turn, can be used in FDA regulated applications such as cell therapy.

In one embodiment of the present invention, a unique process that uses differential cell stress activation and modulation is utilized as a basis for cell selection.

A challenge to medical diagnostics, stem cell therapy and cancer therapy is to selectively eliminate or protect one or more cell types from a mixed population of cancer/non-tumorigenic cells without the use of chemotherapeutic agents or antibodies. Indeed, cancer stem cells are thought to be present in less than 1% of a stem cell population but currently antibodies are required to purify them. Furthermore, the use of human embryonic stem cells (hESCs) and induced pluripotent stem cells (iPSCs) for cell therapy will ultimately require selective elimination of the small number of tumorigenic undifferentiated cells known to be present in these populations. While the use of cytotoxic monoclonal antibodies and other transfection systems are currently being tested to address this problem, neither are consistent with FDA regulations for cell therapy. Also, the ability to selectively eliminate cancer cells in a cell culture setting using mutagenic, chemotherapeutic compounds is the basis of cancer drug discovery. This approach typically requires the use of DNA binding drugs and/or tumor suppressor activators that can not be used in any procedure that ultimately results in the transfusion of cell products into patients. One embodiment of the invention enables the targeted selection of cell populations from a mixed population based on the inhibiting select cell stress pathways in targeted cell populations followed by exposure to a unique stress regime. This has broad based application in the selection of normal vs. cancer cell types, where cell selection system can be used for a variety of applications where the selection of a desired cell phenotype is desired (See FIG. 1C).

Other applications include the isolation of stem cell populations from tissue samples, purification of other cells from tissues and organs, sorting of unique genetic variants of cells among others. This technology can be applied in a diversity of applications and products including in stem cell therapy, regenerative medicine, cell diagnostics and cancer treatment. In summary, the differential response of inducibly-triggered, cell stress pathways underlying cell select concept may ultimately serve as a method of cell selection that could have a broad application to the field of cell bioprocessing, cancer stem cell research, future hESC and iPSC cell therapy, diagnostics and cancer therapy.

While the ability to create highly differentiated cells from both hESC and iPSC is now well established, the largest problem for the use of these cells in cell therapy and regenerative medicine is the demonstrated fact that they produce teratomas in situ. This has prompted a few groups to call for some type of cell selection or in vitro optimization process that selectively eliminates the tumorigenic iPSC and hESC in a mixed population. This technique could be used to selectively eliminate tumorigenic iPSCs and hESCs on the path to make these cells safer for cell therapy. Further, such a technology could also have tremendous impact as a means to select out low abundance cancer stem cells and other rate tumorigenic cells in tumors for further analysis, culture propagation research, etc.

The innovative novel development of cell select is that there is no report in the literature that cell specific responses to distinct laboratory based stress regimes can be used as a cell selection paradigm. While cell select is not an antibody based selection system as is the case with most other cell identification systems used with FACS, etc., it is, however, specific given that it targets differences in cell stress pathways rather than cell surface markers. Cell select is an in situ, culture/bioprocessing based cell selection reagent which will allow for the rapid purification of sub-populations of cells without the use of complex costly time consuming equipment and procedures. Furthermore, given that it is an antibody-free system, no external proteins are introduced into the mixed cell culture and, as such, Cell select might be more amenable to FDA approval as a cell selection process for stem cell therapy. Beyond in vitro selection, one forward looking potential downstream application of cell select is in the clinical setting.

For instance, if the stress pathway activator tunicamycin can selectively kill basal cell carcinoma cells but not NHEK, then this type of approach would provide a foundation for a topical, adjunctive, clinical treatment for skin basal cell carcinoma. Finally, it is possible that a tandem series of different cell stress pathway paradigms used with a mixed cell group could uncover rare low abundance cell types never previously identified that may be of pharmaceutical and basic research interest.

Cell Selection Data

An underlying premise of the research is that stress response is cell-type specific. Targeted caspase inhibition can have a positive effect in various systems that include cells such as fibroblasts, hepatocytes, renal cells, PBMC's, corneal cells, cardiomyocytes, embryonic stem cells, and mesenchymal stem cells among others. Additional studies focus on the impact of the AKT and mitochondrial stress response pathways during cornea cell isolation and manipulation. These experiments demonstrate that targeted modulation of AKT and the mitochondrial permeability transition pore (MPTP) using cyclosporine A results in a reduction in cell stress response and an increased maintenance of viability. Further, studies using vitamin $D_3$ and antioxidants (e.g. resveratrol) have also yielded data supporting the concept of maintaining cell quality in these and other cell types during processing. More recent data suggest that the unfolding protein response (UPR) may also be activated in response to stress in human hepatocytes, as the inclusion of salubrinal, a UPR inhibitor, improved cellular tolerance to thermal challenge.

Figure 18:
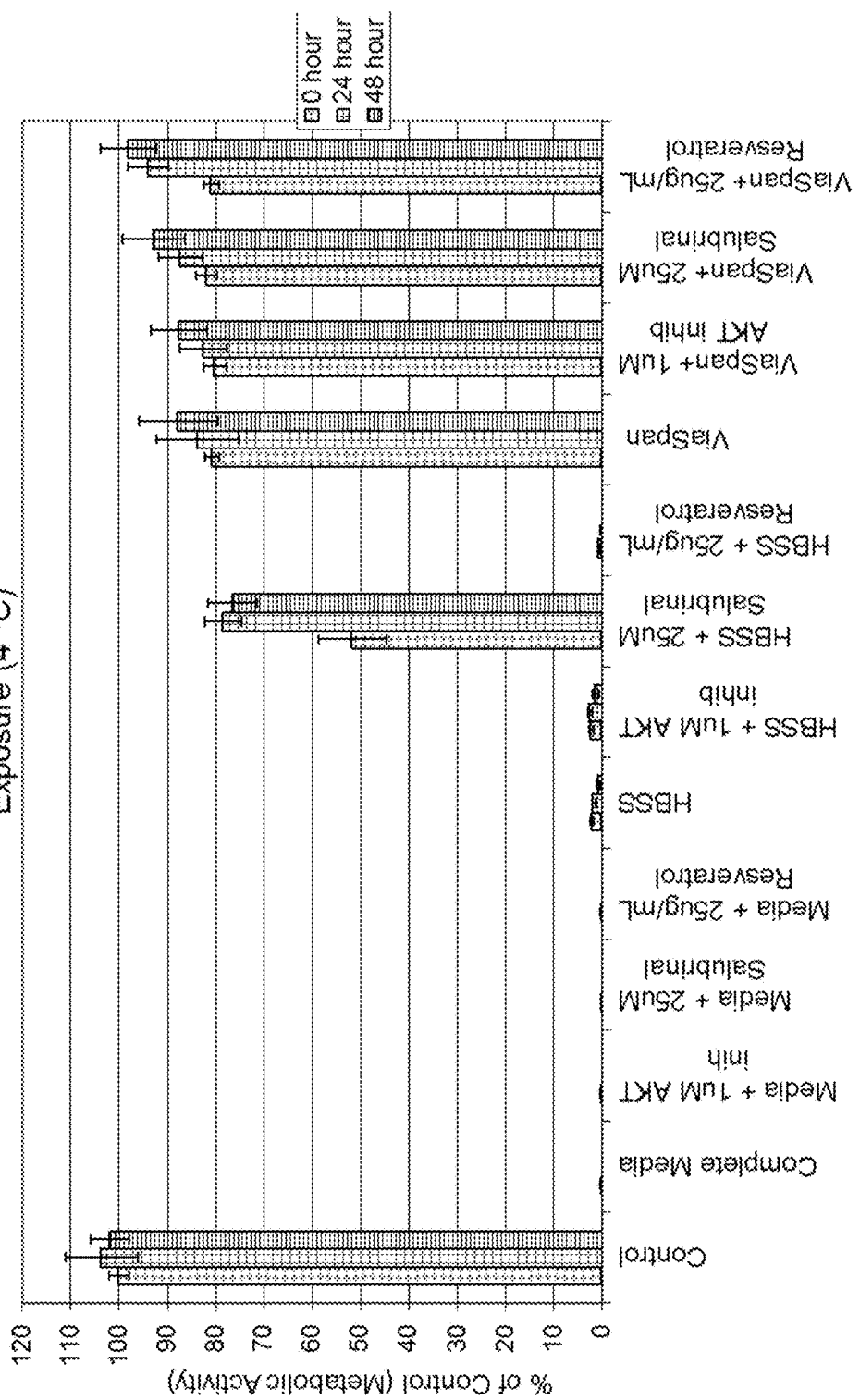
FIG. 18 is a graphical depiction of the viability of C3A, human liver cancer cells, following two days of hypothermic exposure at 4° C.

The phenomena of stress based cell selection is exemplified in a series of experiments where the liver cancer cell line, C3A, was exposed to a thermal stress regime in a variety of carrier media supplemented with either salubrinal or resveratrol. The data in FIG. 18 show that the UPR inhibitor, salubrinal, but not resveratrol or the AKT inhibitor, were able to maintain the cells during cold stress exposure. Application of the stress modulation model to cultures of normal rat hepatocytes in FIG. 19 demonstrates that salubrinal failed to protect the cells where resveratrol did. This represented an exact opposite effect as seen in the cancerous C3A cells. Further, as shown in FIG. 20, normal human hepatocytes were subjected to the same thermal stress paradigm and yielded similar results to the normal rat hepatocyte data. Again, in contrast to C3A cells, resveratrol (FR-48), but not salubrinal, was able to completely maintain primary human hepatocytes subjected to thermal stress.

The utilization of cell stress response modulation based cell selection has also been demonstrated in a number of other stress models including normothermic incubation/storage, hypoxia, anoxia, physical manipulation, nutrient deprivation and pH alteration among others. As an example, hepatocytes and C3A cells were placed under hypoxic conditions at room temperature (normothermic incubation) in various commercial media with and without salubrinal or resveratrol. See FIGS. 10A, 10B, 10C, 10D. As with the cold thermal stress model, through the application of the current invention, preferential selection of either cell population was possible. The table in FIG. 10 summarizes the representative response of the various liver cells when placed into the two stress model conditions of thermal and hypoxic stress.

Figure 16:
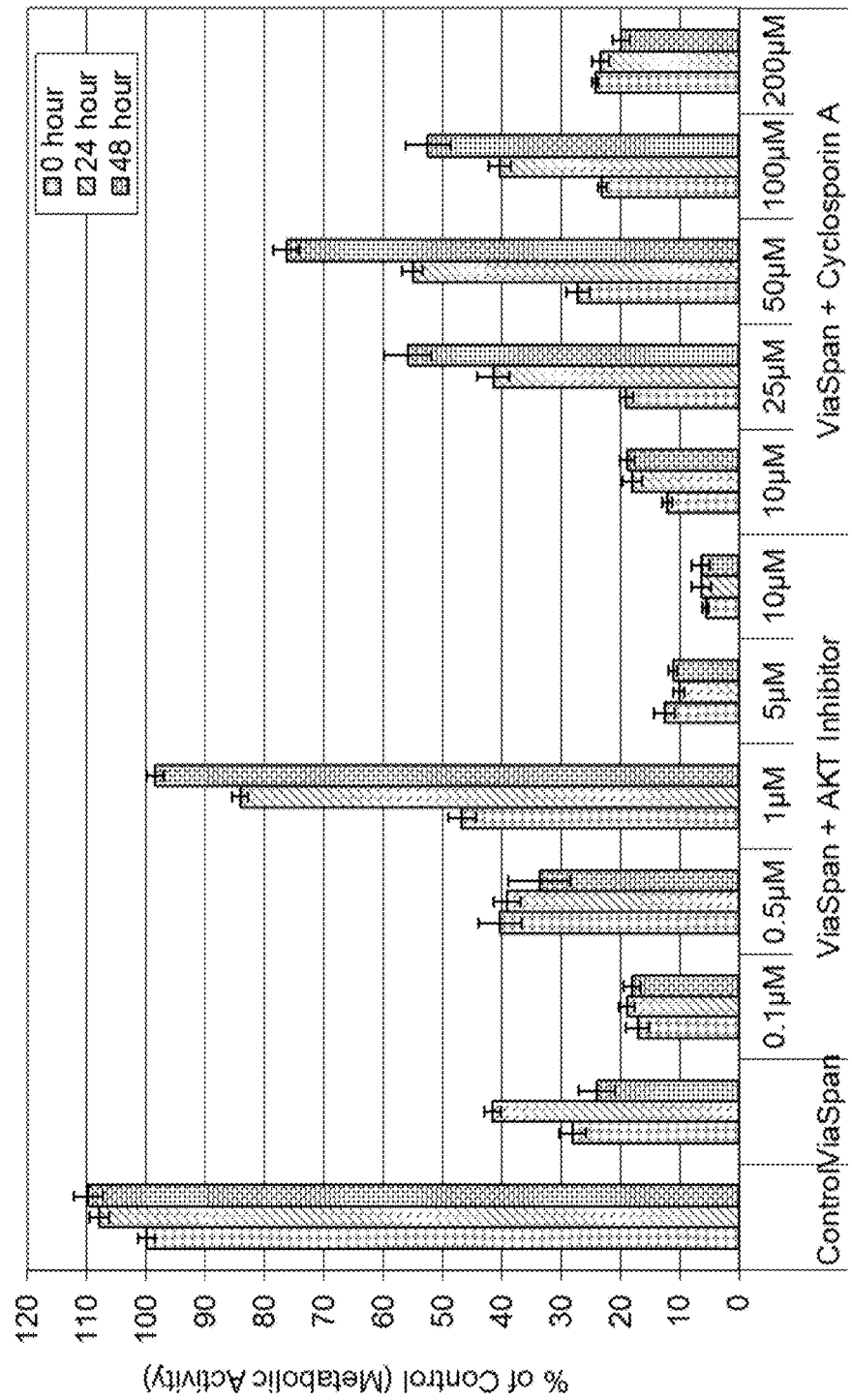
FIG. 16 demonstrates the viability of HCECs following 7 days of hypothermic exposure.
Figure 17:
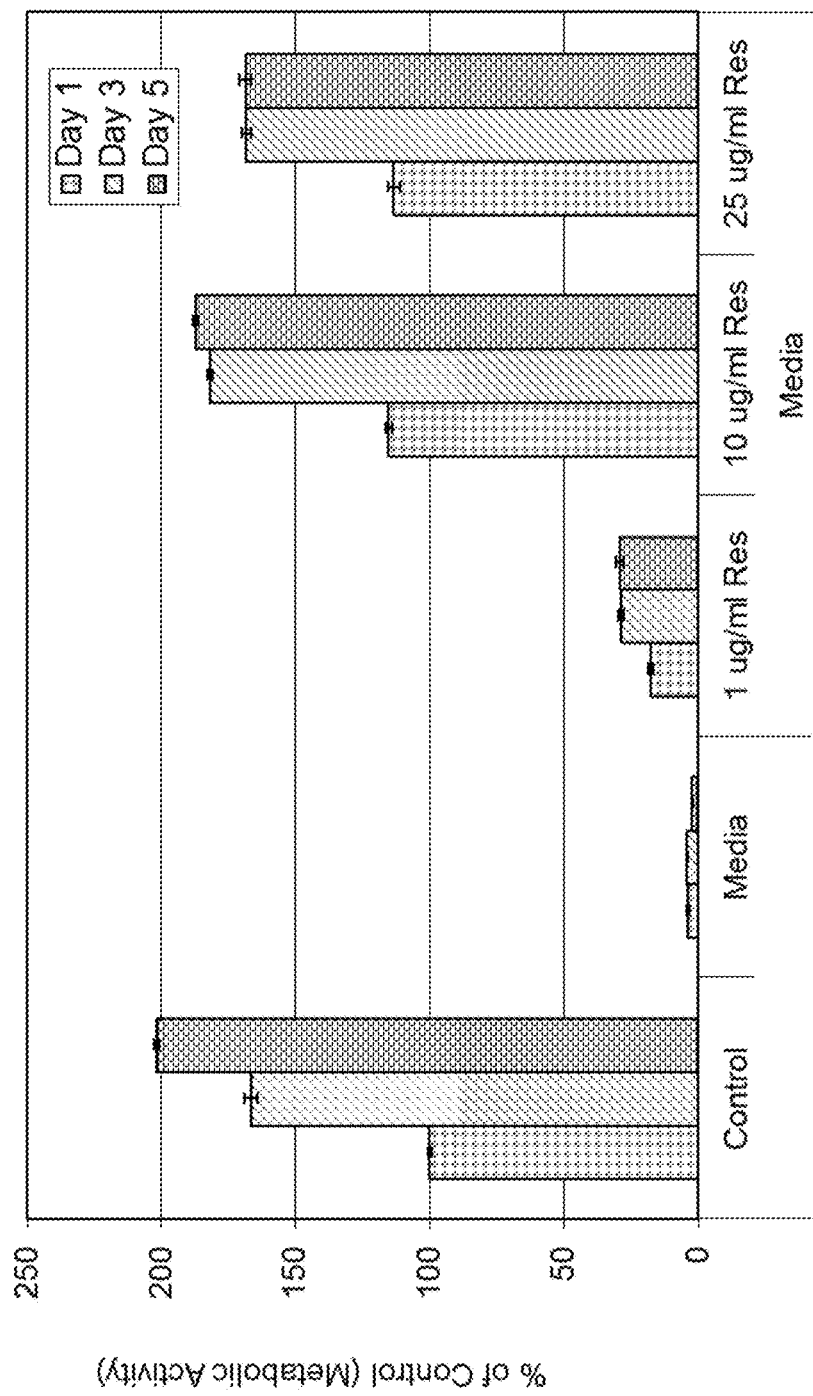
FIG. 17 shows the viability of HCECs following 2 days of hypothermic exposure.

As shown in FIG. 16, the experiments demonstrated that targeted modulation of AKT and the mitochondrial permeability transition pore (MPTP) using cyclosporine A resulted in a reduction in cell stress response and an increased maintenance of viability. Further, studies using vitamin $D_3$ (data not shown) and antioxidants (e.g. resveratrol (Res), FIG. 17) have also yielded data supporting the concept of maintaining cell quality in these and other cell types during processing. More recent data suggest that the unfolding protein response (UPR) may also be activated in response to stress in human hepatocytes, as the inclusion of salubrinal, a UPR inhibitor, improved cellular responses to thermal challenge. Thus, a variety of cell stress pathways may be activated when cells are exposed to a hypothermic stress.

In FIG. 18, the hepatoma cell line, C3A, was exposed to CPSI's hypothermic stress regime in a variety of carrier media supplemented with either salubrinal or resveratrol. The data in FIG. 18 show that the UPR inhibitor, salubrinal, but not resveratrol or the AKT inhibitor, were able to protect human cells from hypothermia-induced cell death. Furthermore, neither salubrinal nor resveratrol appeared to be toxic when in the presence of the organ storage solution, ViaSpan.

Figure 19:
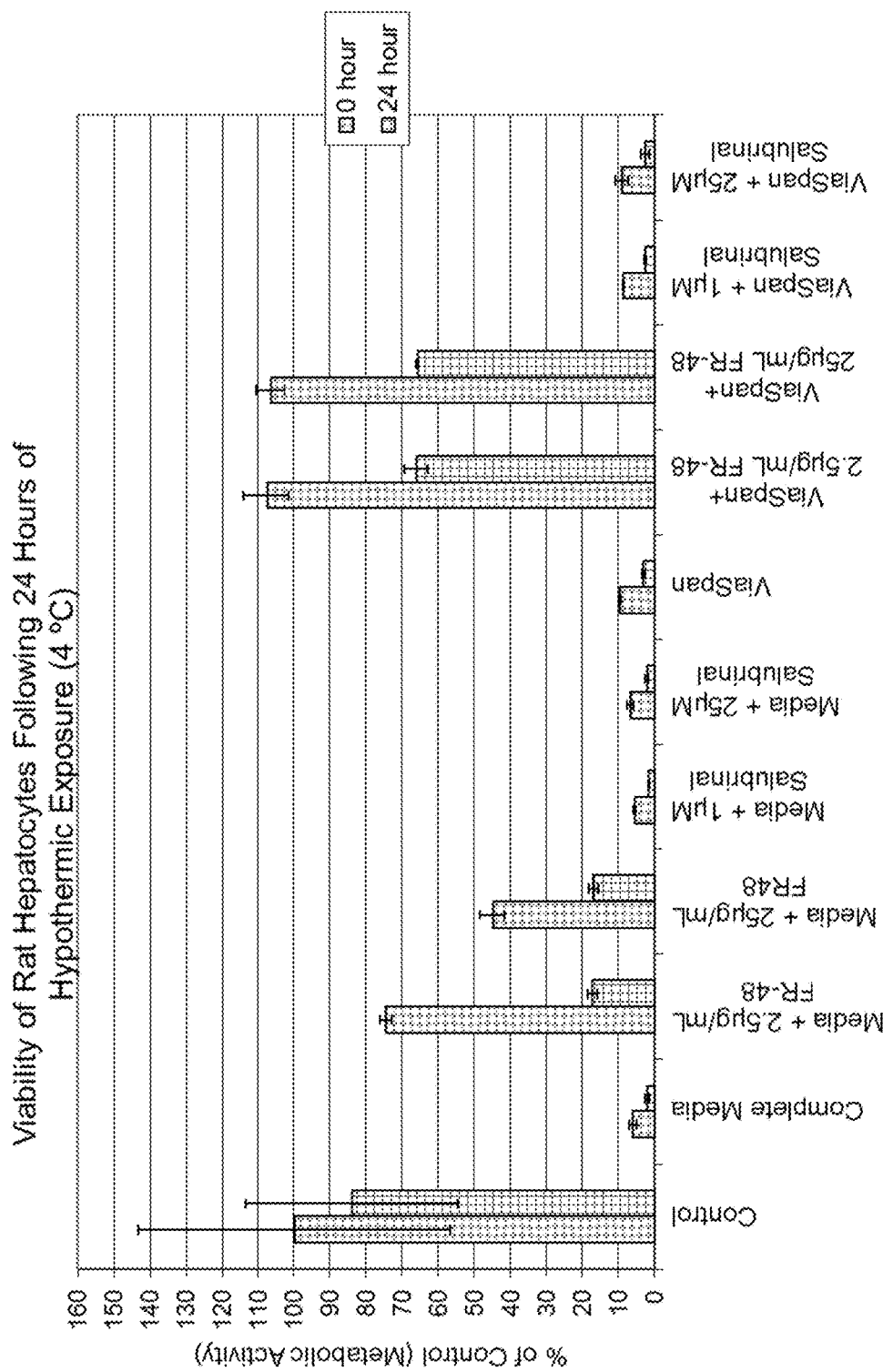
FIG. 19 is the depiction of the viability of rat hepatocytes following 24 hours of hypothermic exposure at 4° C.
Figure 20:
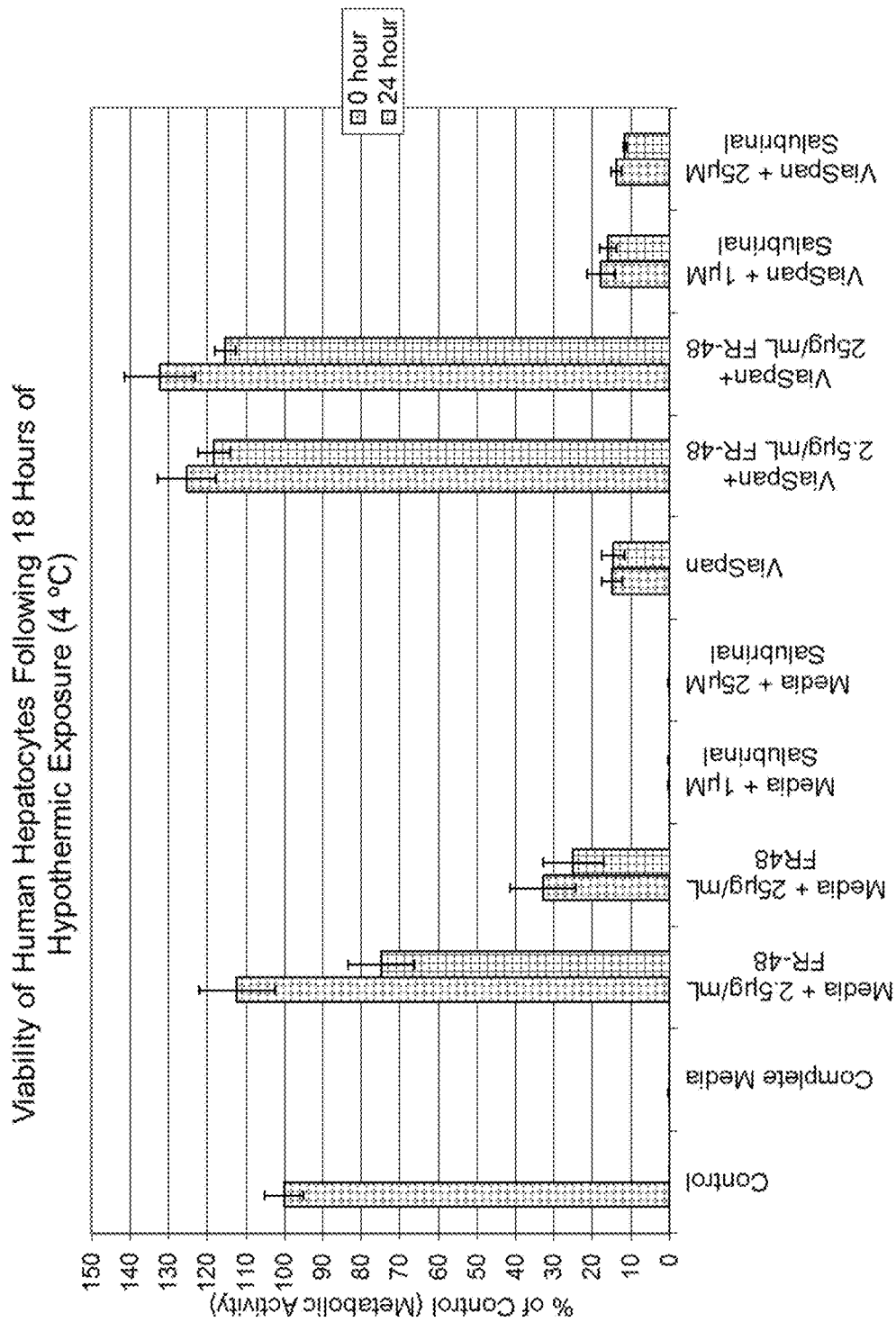
FIG. 20 depicts the viability of human hepatocytes following 18 hours of hypothermic exposure at 4° C.

In FIG. 19, the C3A cells were then substituted with rat primary hepatocytes. In this case, salubrinal failed to protect these cells from hypothermic stress but resveratrol very effectively protected rat primary hepatocytes from cell death (See FIG. 19). The results were attributed to the difference in species origin of the cells.

As such, in FIG. 20, primary human hepatocytes were then subjected to the same hypothermic stress paradigm. Results were similar to those of rat hepatocytes. In contrast to C3A cells, resveratrol (FR-48), but not salubrinal, was able to completely protect primary human hepatocytes subjected to cold stress.

In Conclusion

In utilizing the cell culture media supplement(s) and methods of molecular stress control of the present invention, various supplements and methods in the industry may be employed in accordance with accepted bioprocessing and bioreactor mass cell culture. As discussed, the embodiments of the invention are for exemplary purposes only and not limitation. Advantageously, this media supplement is utilized at normothermic temperatures as standardized or optimized for cell growth, maintenance and sustenance. The methods for maintaining mass cell cultures for further research and clinical use represents an important step in therapeutic discovery. Though the cell culture media supplement and method of use has been developed to enable and improve some of the approaches used to characterize, analyze, and purify cell cultures, other therapeutic measures may integrally make use of the supplement, simultaneously during the stress pathway or post-stress recovery.

In one embodiment, hypothermic stress regimes are utilized. In another embodiment, normothermic conditions are utilized while other stressors are tested in the processing.

For exemplary purposes, and not limitation, the following stress models/regimes have been tested and demonstrated in the above illustrations.

Stress Regime 1—Mechanical: Cells or tissues were harvested and cultured, split and vortexed for 30 to 60 sec resulting in 30% cell death at 24 hrs compared to non-vortexed samples. This procedure is designed to model various mechanical manipulation steps involved in cell processing.

Stress Regime 2—Hypoxia: Cells were held at 37° C. in an incubator with reduced levels of $O_2$ for a 24 hour period. Two hypoxia models were utilized including increased $CO_2$ levels providing for an 80% air: 20% $CO_2$ ratio (versus standard 95% air: 5% $CO_2$) as well as limited gas exchange using isolated environmental chambers. This procedure is designed to model various intervals of suboptimal culture conditions associated with cell processing and utilization.

Stress Regime 3—Thermal Fluctuations: Cells were subjected to cold exposure (4° C.) following SOP and then returned to normothermic conditions.

Various stress regimes may be further employed that may target specific molecular pathways, prevent apoptosis, and/or sustain cells during a multitude of bioprocessing events.

Thus, the invention may facilitate other improvements in diagnosis, pathology, and/or treatment screening, including its use in fields of cell/gene therapy, drug discovery, and/or cryotherapy or thermal ablation, such medical devices or components associated with the treatments. The invention facilitates the molecular pathway characterization and the translational science for cellular-based therapeutic developments.

Embodiments of the invention comprise manipulation of cell stress response pathways to maintain both the viability and function of cells during bioprocessing. Further, the technology can be utilized to selectively eliminate or purify sub-populations of cells within a heterogenous population (e.g. normal cells vs. cancer cells, different cell lines, etc). In one aspect, suppressing cell stress pathways can maintain cells under stress regimes. In another aspect, activating cell stress pathways can work in conjunction with enhanced therapeutic outcomes (e.g. cancer treatment or atrial fibrillation) such as in the case where cryoablation is utilized.

The embodiments of the invention may be modified to take the form of any analog or derivative therefrom. As presented, multiple embodiments of the invention offer several improvements over standard cell culture bioprocessing. The previously unforeseen benefits have been realized and conveniently offer advantages for the treatment of multiple disease states. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

We claim:

1. A cell selection method comprising the steps of:
    applying a cell selection reagent to an in vitro heterogeneous population of cells, wherein the heterogeneous population of cells includes at least a first population of cancerous mammalian hepatic cells and a second population of non-cancerous mammalian hepatic cells, and the cell selection reagent is an unfolded protein response (UPR) pathway inhibitor or a UPR pathway inducer; and
    exposing the heterogeneous population of cells to a stress regimen, wherein the stress regimen produces a cell-type specific stress response in the heterogeneous population of cells, and wherein the cell selection reagent selectively modulates the UPR pathway in a cell-type specific manner in one of the first population of cancerous hepatic cells or the second population of non-cancerous hepatic cells to confer protection from the stress regimen,
    wherein the cell selection method is performed according to one of the following sets of parameters:
    a) the cell selection reagent is salubrinal, the stress regimen includes a hypothermic condition, and the selective modulating extends viability of the first population of cancerous mammalian hepatic cells, or
    b) the cell selection reagent is resveratrol (FR-48), the stress regimen includes a hypothermic condition, and the selective modulating extends viability of the second population of non-cancerous mammalian hepatic cells, or
    c) wherein the cell selection reagent is salubrinal, the stress regimen includes hypoxic, normothermic storage, and the selective modulating extends viability of the second population of non-cancerous mammalian hepatic cells.

2. A method of eliminating a selected cell population in an in vitro heterogeneous cell population, the method comprising:
    applying salubrinal to the heterogeneous population of cells, and the heterogeneous population of cells includes a first population of cancerous mammalian hepatic cells to be maintained, and a second population of non-cancerous mammalian hepatic cells to be eliminated; and
    exposing the heterogeneous cell population to a hypothermic condition,
    wherein the cell selection reagent selectively modulates and reduces a response to the stress regimen in the first population of cancerous mammalian hepatic cells to be maintained, and does not reduce the response to the stress regimen in the second population of non-cancerous mammalian hepatic cells to be eliminated,
    wherein the reducing of the response to the stress regimen has a protective effect on the first population of cancerous mammalian hepatic cells to be maintained relative to the second population of non-cancerous mammalian hepatic cells to be eliminated, and
    wherein exposure to the stress regimen selectively kills the second population of non-cancerous mammalian hepatic cells to be eliminated.

3. The method of claim 1, wherein the cell selection method is performed according to parameter set a), and
    the salubrinal selectively inhibits the UPR pathway in the first population of cancerous mammalian hepatic cells, and either does not inhibit the UPR pathway in the second population of non-cancerous mammalian hepatic cells, or the salubrinal inhibits the UPR pathway in the second population of non-cancerous mammalian hepatic cells to a lesser degree than the first population of mammalian cancerous hepatic cells.

4. The method of claim 1, wherein the cell selection method is performed according to parameter set b), and
    the resveratrol (FR-48) selectively induces the UPR pathway in the second population of non-cancerous mammalian hepatic cells, and either does not induce the UPR pathway in the first population of cancerous mammalian hepatic cells, or the resveratrol (FR-48) induces the UPR pathway in the first population of cancerous mammalian hepatic cells to a lesser degree than the second population of non-cancerous mammalian hepatic cells.

5. The method of claim 1, wherein the cell selection method is performed according to parameter set c), and the salubrinal selectively inhibits the UPR pathway in the second population of non-cancerous mammalian hepatic cells, and either does not inhibit the UPR pathway in the first population of cancerous mammalian hepatic cells, or the salubrinal inhibits the UPR pathway in the first population of cancerous mammalian hepatic cells to a lesser degree than the second population of non-cancerous mammalian hepatic cells.

6. The method of claim 1, wherein the cancerous mammalian hepatic cells are liver cancer cell line C3A cells, and the non-cancerous mammalian hepatic cells are rat or human hepatocytes.

7. The method of claim 2, wherein the first population of cancerous mammalian hepatic cells to be maintained are liver cancer cell line C3A cells, and the second population of non-cancerous mammalian hepatic cells to be eliminated are rat or human hepatocytes.

8. A cell selection method comprising the steps of:
applying resveratrol (FR-48) to an in vitro heterogeneous cell population, wherein the heterogeneous cell population includes at least a first population of cancerous mammalian hepatic cells and a second population of non-cancerous mammalian hepatic cells; and
exposing the heterogeneous cell population to a hypothermic condition, wherein the hypothermic condition produces a cell-type specific stress response in the heterogeneous cell population,
wherein the resveratrol (FR-48) selectively modulates at least one of a UPR pathway or an oxidative stress response pathway in a cell-type specific manner in the second population of non-cancerous mammalian hepatic cells, thereby conferring protection from the hypothermic condition on, and extending viability of the second population of non-cancerous mammalian hepatic cells.

9. The method of claim 8, wherein the second population of non-cancerous mammalian hepatic cells are rat or human hepatocytes, and the first population of cancerous mammalian hepatic cells are liver cancer cell line C3A cells.

* * * * *